United States Patent
Von Segesser et al.

(10) Patent No.: US 9,216,082 B2
(45) Date of Patent: Dec. 22, 2015

(54) STENT-VALVES FOR VALVE REPLACEMENT AND ASSOCIATED METHODS AND SYSTEMS FOR SURGERY

(75) Inventors: Ludwig K. Von Segesser, Lausanne (CH); Stéphane Delaloye, Bülach (CH)

(73) Assignee: Symetis SA, Ecublens VD (CH)

( * ) Notice: Subject to any disclaimer, the term of this patent is extended or adjusted under 35 U.S.C. 154(b) by 838 days.

(21) Appl. No.: 12/401,329

(22) Filed: Mar. 10, 2009

(65) Prior Publication Data

US 2009/0171432 A1    Jul. 2, 2009

Related U.S. Application Data

(62) Division of application No. 11/700,922, filed on Dec. 21, 2006, now abandoned.

(60) Provisional application No. 60/753,071, filed on Dec. 22, 2005, provisional application No. 60/755,590, filed on Dec. 29, 2005, provisional application No. 60/843,181, filed on Sep. 7, 2006.

(51) Int. Cl.
*A61F 2/24*     (2006.01)
*A61F 2/95*     (2013.01)
*A61F 2/966*    (2013.01)

(52) U.S. Cl.
CPC ............... *A61F 2/2418* (2013.01); *A61F 2/243* (2013.01); *A61F 2/2427* (2013.01); *A61F 2/2433* (2013.01); *A61F 2/2436* (2013.01); *A61F 2/2472* (2013.01); *A61F 2002/9505* (2013.01); *A61F 2002/9522* (2013.01); *A61F 2002/9534* (2013.01); *A61F 2002/9665* (2013.01);

(Continued)

(58) Field of Classification Search
CPC ............... A61F 2/2427; A61F 2/2439; A61F 2002/9505; A61F 2002/9522; A61F 2002/9534; A61F 2002/9665
USPC ............................ 623/1.11, 1.12, 2.11–2.19
See application file for complete search history.

(56) References Cited

U.S. PATENT DOCUMENTS 3,755,823 A    9/1973    Hancock
4,106,129 A    8/1978    Carpentier et al.

(Continued)

FOREIGN PATENT DOCUMENTS

AU    2006328896    3/2008
AU    2007294199    6/2008

(Continued)

OTHER PUBLICATIONS

Machine Translation of WO 2006/076890, http://translationportal.epo.org/emtp/translate/?ACTION=description-retrieval&COUNTRY=WO&FORMAT=docdb&kind=A1&locale=en_EP&number=2006076890&OPS=ops.epo.org&engine=google&srclang=de&trglang=en, 8 pages, printed Apr. 17, 2012.*

(Continued)

*Primary Examiner* — Thomas J Sweet
*Assistant Examiner* — Cheryl Miller
(74) *Attorney, Agent, or Firm* — Cooley LLP; Brian P. Hopkins

(57) ABSTRACT

Stent-valves (e.g., single-stent-valves and double-stent-valves), associated methods and systems for their delivery via minimally-invasive surgery, and guide-wire compatible closure devices for sealing access orifices are provided.

37 Claims, 32 Drawing Sheets

(52) U.S. Cl.
CPC . *A61F2210/0014* (2013.01); *A61F 2210/0042* (2013.01); *A61F 2220/0016* (2013.01); *A61F 2220/0075* (2013.01); *A61F 2220/0083* (2013.01); *A61F 2230/0013* (2013.01); *A61F 2230/0067* (2013.01); *A61F 2230/0078* (2013.01); *A61F 2250/001* (2013.01); *A61F 2250/006* (2013.01); *A61F 2250/0039* (2013.01)

(56) References Cited

U.S. PATENT DOCUMENTS

| | | | |
|---|---|---|---|
| 4,470,157 A | 9/1984 | Love | |
| 5,078,720 A | 1/1992 | Burton et al. | |
| 5,163,955 A | 11/1992 | Love et al. | |
| 5,192,301 A | 3/1993 | Kamiya et al. | |
| 5,272,909 A | 12/1993 | Nguyen | |
| 5,327,774 A | 7/1994 | Nguyen | |
| 5,344,442 A | 9/1994 | Deac | |
| 5,354,330 A | 10/1994 | Hanson | |
| 5,411,552 A | 5/1995 | Andersen | |
| 5,480,424 A | 1/1996 | Cox | |
| 5,487,760 A | 1/1996 | Villafana | |
| 5,499,995 A | 3/1996 | Teirstein | |
| 5,500,015 A | 3/1996 | Deac | |
| 5,540,712 A | 7/1996 | Kleshinski et al. | |
| 5,554,185 A | 9/1996 | Block | |
| 5,569,274 A | 10/1996 | Rapacki | |
| 5,571,174 A | 11/1996 | Love et al. | |
| 5,571,215 A | 11/1996 | Sterman | |
| 5,609,626 A | 3/1997 | Quijano | |
| 5,653,749 A | 8/1997 | Love et al. | |
| 5,662,703 A | 9/1997 | Yurek | |
| 5,682,906 A | 11/1997 | Sterman | |
| 5,713,950 A | 2/1998 | Cox | |
| 5,713,951 A | 2/1998 | Garrison | |
| 5,718,725 A | 2/1998 | Sterman | |
| 5,728,151 A | 3/1998 | Garrison | |
| 5,746,765 A * | 5/1998 | Kleshinski et al. | 128/898 |
| 5,769,882 A | 6/1998 | Fogarty et al. | |
| 5,797,960 A | 8/1998 | Stevens | |
| 5,799,661 A | 9/1998 | Boyd | |
| 5,807,327 A | 9/1998 | Green | |
| 5,814,016 A | 9/1998 | Valley | |
| 5,817,126 A | 10/1998 | Imran | |
| 5,823,956 A | 10/1998 | Roth | |
| 5,824,041 A | 10/1998 | Lenker | |
| 5,824,061 A | 10/1998 | Quijano | |
| 5,824,063 A | 10/1998 | Cox | |
| 5,829,447 A | 11/1998 | Stevens | |
| 5,840,081 A | 11/1998 | Andersen | |
| 5,855,210 A | 1/1999 | Sterman | |
| 5,855,600 A | 1/1999 | Alt | |
| 5,855,601 A | 1/1999 | Bessler | |
| 5,861,028 A | 1/1999 | Angell | |
| 5,924,424 A | 7/1999 | Stevens | |
| 5,938,697 A | 8/1999 | Killion et al. | |
| 5,957,949 A | 9/1999 | Leonhardt | |
| 5,976,174 A | 11/1999 | Ruiz | |
| 5,980,455 A | 11/1999 | Daniel | |
| 5,980,533 A * | 11/1999 | Holman | 623/1.11 |
| 5,997,573 A | 12/1999 | Quijano | |
| 6,010,531 A | 1/2000 | Donlon | |
| 6,027,476 A | 2/2000 | Sterman | |
| 6,029,671 A | 2/2000 | Stevens | |
| 6,079,414 A | 6/2000 | Roth | |
| 6,083,257 A | 7/2000 | Taylor et al. | |
| 6,092,529 A | 7/2000 | Cox | |
| 6,110,191 A | 8/2000 | Dehdashtian | |
| 6,110,201 A | 8/2000 | Quijano | |
| 6,125,852 A | 10/2000 | Stevens | |
| 6,168,614 B1 | 1/2001 | Andersen | |
| 6,171,335 B1 | 1/2001 | Wheatley | |
| 6,182,664 B1 | 2/2001 | Cosgrove | |
| 6,183,481 B1 | 2/2001 | Lee | |
| 6,196,230 B1 | 3/2001 | Hall | |
| 6,214,036 B1 | 4/2001 | Letendre et al. | |
| 6,245,105 B1 | 6/2001 | Nguyen | |
| 6,254,564 B1 | 7/2001 | Wilk | |
| 6,270,526 B1 | 8/2001 | Cox | |
| 6,283,127 B1 | 9/2001 | Sterman | |
| 6,287,334 B1 | 9/2001 | Moll | |
| 6,287,339 B1 | 9/2001 | Vazquez | |
| 6,311,693 B1 | 11/2001 | Sterman | |
| 6,325,067 B1 | 12/2001 | Sterman | |
| 6,331,189 B1 | 12/2001 | Wolinsky | |
| 6,346,074 B1 | 2/2002 | Roth | |
| 6,350,278 B1 | 2/2002 | Lenker | |
| 6,378,221 B1 | 4/2002 | Ekholm | |
| 6,379,372 B1 | 4/2002 | Dehdashtian | |
| 6,379,383 B1 | 4/2002 | Palmaz | |
| 6,401,720 B1 | 6/2002 | Stevens | |
| 6,406,493 B1 | 6/2002 | Tu | |
| 6,409,759 B1 | 6/2002 | Peredo | |
| 6,451,054 B1 | 9/2002 | Stevens | |
| 6,454,799 B1 | 9/2002 | Schreck | |
| 6,458,153 B1 | 10/2002 | Bailey | |
| 6,494,211 B1 | 12/2002 | Boyd | |
| 6,494,897 B2 | 12/2002 | Sterman | |
| 6,530,952 B2 | 3/2003 | Vesely | |
| 6,533,807 B2 | 3/2003 | Wolinsky | |
| 6,537,310 B1 | 3/2003 | Palmaz | |
| 6,558,318 B1 | 5/2003 | Daniel | |
| 6,562,069 B2 | 5/2003 | Cai et al. | |
| 6,564,805 B2 | 5/2003 | Garrison | |
| 6,569,196 B1 | 5/2003 | Vesely | |
| 6,572,652 B2 | 6/2003 | Shaknovich | |
| 6,582,462 B1 | 6/2003 | Andersen | |
| 6,589,279 B1 | 7/2003 | Anderson | |
| 6,605,112 B1 | 8/2003 | Moll | |
| 6,613,069 B2 | 9/2003 | Boyd | |
| 6,613,079 B1 | 9/2003 | Wolinsky | |
| 6,635,085 B1 | 10/2003 | Caffey | |
| 6,651,672 B2 | 11/2003 | Roth | |
| 6,652,555 B1 | 11/2003 | VanTassel et al. | |
| 6,652,578 B2 | 11/2003 | Bailey | |
| 6,673,109 B2 | 1/2004 | Cox | |
| 6,679,268 B2 | 1/2004 | Stevens | |
| 6,682,558 B2 | 1/2004 | Tu | |
| 6,682,559 B2 | 1/2004 | Myers | |
| 6,692,512 B2 | 2/2004 | Jang | |
| 6,695,865 B2 | 2/2004 | Boyle | |
| 6,695,875 B2 * | 2/2004 | Stelter et al. | 623/1.13 |
| 6,719,787 B2 | 4/2004 | Cox | |
| 6,719,788 B2 | 4/2004 | Cox | |
| 6,719,789 B2 | 4/2004 | Cox | |
| 6,723,122 B2 | 4/2004 | Yang | |
| 6,730,118 B2 | 5/2004 | Spenser | |
| 6,733,513 B2 | 5/2004 | Boyle | |
| 6,733,525 B2 | 5/2004 | Yang et al. | |
| 6,736,827 B1 | 5/2004 | McAndrew | |
| 6,736,846 B2 | 5/2004 | Cox | |
| 6,755,855 B2 | 6/2004 | Yurek | |
| 6,767,362 B2 | 7/2004 | Schreck | |
| 6,790,229 B1 | 9/2004 | Berreklouw | |
| 6,802,319 B2 | 10/2004 | Stevens et al. | |
| 6,805,711 B2 | 10/2004 | Quijano | |
| 6,820,676 B2 | 11/2004 | Palmaz | |
| 6,830,584 B1 | 12/2004 | Seguin | |
| 6,830,585 B1 | 12/2004 | Artof | |
| 6,830,586 B2 | 12/2004 | Quijano | |
| 6,849,085 B2 | 2/2005 | Marton | |
| 6,872,226 B2 | 3/2005 | Cali | |
| 6,875,231 B2 | 4/2005 | Anduiza | |
| 6,881,199 B2 | 4/2005 | Wilk | |
| 6,893,460 B2 | 5/2005 | Spenser | |
| 6,899,704 B2 | 5/2005 | Sterman | |
| 6,908,481 B2 | 6/2005 | Cribier | |
| 6,911,043 B2 | 6/2005 | Myers | |
| 6,936,066 B2 | 8/2005 | Palmaz | |
| 6,939,359 B2 | 9/2005 | Tu | |
| 6,942,682 B2 | 9/2005 | Vrba | |
| 6,955,175 B2 | 10/2005 | Stevens | |
| 6,974,464 B2 | 12/2005 | Quijano | |

(56) References Cited

U.S. PATENT DOCUMENTS

| | | |
|---|---|---|
| 6,979,350 B2 | 12/2005 | Moll |
| 7,018,406 B2 | 3/2006 | Seguin |
| 7,018,408 B2 | 3/2006 | Bailey |
| 7,022,134 B1 | 4/2006 | Quijano |
| 7,025,773 B2 | 4/2006 | Gittings |
| 7,025,780 B2 | 4/2006 | Gabbay |
| 7,028,692 B2 | 4/2006 | Sterman |
| 7,037,333 B2 | 5/2006 | Myers |
| 7,041,132 B2 | 5/2006 | Quijano |
| 7,044,966 B2 | 5/2006 | Svanidze |
| 7,048,757 B2 | 5/2006 | Shaknovich |
| 7,101,396 B2 | 9/2006 | Artof |
| 7,118,585 B2 | 10/2006 | Addis |
| 7,141,064 B2 | 11/2006 | Scott |
| 7,179,290 B2 | 2/2007 | Cao |
| 7,195,641 B2 | 3/2007 | Palmaz |
| 7,198,646 B2 | 4/2007 | Figulla |
| 7,201,772 B2 | 4/2007 | Schwammenthal et al. |
| 7,214,344 B2 | 5/2007 | Carpentier |
| 7,217,287 B2 | 5/2007 | Wilson |
| 7,235,092 B2 | 6/2007 | Banas |
| 7,252,682 B2 | 8/2007 | Seguin |
| 7,276,078 B2 | 10/2007 | Spenser |
| 7,276,084 B2 | 10/2007 | Yang |
| 7,285,130 B2 | 10/2007 | Austin |
| 7,314,449 B2 | 1/2008 | Pfeiffer |
| 7,314,485 B2 | 1/2008 | Mathis |
| 7,314,880 B2 | 1/2008 | Chang |
| 7,316,712 B2 | 1/2008 | Peredo |
| 7,317,005 B2 | 1/2008 | Hoekstra |
| 7,317,942 B2 | 1/2008 | Brown |
| 7,317,950 B2 | 1/2008 | Lee |
| 7,318,278 B2 | 1/2008 | Zhang |
| 7,319,096 B2 | 1/2008 | Malm |
| 7,320,692 B1 | 1/2008 | Bender |
| 7,320,704 B2 | 1/2008 | Lashinski |
| 7,320,705 B2 | 1/2008 | Quintessenza |
| 7,320,706 B2 | 1/2008 | Al-Najjar |
| 7,326,174 B2 | 2/2008 | Cox |
| 7,326,219 B2 | 2/2008 | Mowry |
| 7,327,862 B2 | 2/2008 | Murphy |
| 7,329,278 B2 | 2/2008 | Seguin |
| 7,329,279 B2 | 2/2008 | Haug |
| 7,329,280 B2 | 2/2008 | Bolling |
| 7,329,777 B2 | 2/2008 | Harter |
| 7,331,991 B2 | 2/2008 | Kheradvar |
| 7,331,993 B2 | 2/2008 | White |
| 7,333,643 B2 | 2/2008 | Murphy |
| 7,335,158 B2 | 2/2008 | Taylor |
| 7,335,213 B1 | 2/2008 | Hyde |
| 7,335,490 B2 | 2/2008 | Van Gilst |
| 7,338,484 B2 | 3/2008 | Schoon |
| 7,361,189 B2 | 4/2008 | Case |
| 7,361,190 B2 | 4/2008 | Shaoulian |
| 7,364,588 B2 | 4/2008 | Mathis |
| 7,371,258 B2 | 5/2008 | Woo |
| 7,374,571 B2 | 5/2008 | Pease |
| 7,377,895 B2 | 5/2008 | Spence |
| 7,377,938 B2 | 5/2008 | Sarac |
| 7,377,940 B2 | 5/2008 | Ryan |
| 7,381,210 B2 | 6/2008 | Zarbatany |
| 7,381,218 B2 | 6/2008 | Schreck |
| 7,381,219 B2 | 6/2008 | Salahieh |
| 7,381,220 B2 | 6/2008 | Macoviak |
| 7,389,874 B2 | 6/2008 | Quest |
| 7,390,325 B2 | 6/2008 | Wang |
| 7,393,358 B2 | 7/2008 | Malewicz |
| 7,393,360 B2 | 7/2008 | Spenser |
| 7,396,364 B2 | 7/2008 | Moaddeb |
| 7,399,315 B2 | 7/2008 | Iobbi |
| 7,402,171 B2 | 7/2008 | Osborne |
| 7,404,792 B2 | 7/2008 | Spence |
| 7,404,793 B2 | 7/2008 | Lau |
| 7,410,499 B2 | 8/2008 | Bicer |
| 7,412,274 B2 | 8/2008 | Mejia |
| 7,412,290 B2 | 8/2008 | Janke |
| 7,415,861 B2 | 8/2008 | Sokel |
| 7,416,530 B2 | 8/2008 | Turner |
| 7,422,603 B2 | 9/2008 | Lane |
| 7,422,606 B2 | 9/2008 | Ung-Chhun |
| 7,423,032 B2 | 9/2008 | Ozaki |
| 7,426,413 B2 | 9/2008 | Balczewski |
| 7,427,279 B2 | 9/2008 | Frazier |
| 7,427,287 B2 | 9/2008 | Turovskiy |
| 7,427,291 B2 | 9/2008 | Liddicoat |
| 7,430,448 B1 | 9/2008 | Zimmer |
| 7,431,691 B1 | 10/2008 | Wilk |
| 7,431,733 B2 | 10/2008 | Knight |
| 7,435,059 B2 | 10/2008 | Smith |
| 7,435,257 B2 | 10/2008 | Lashinski |
| 7,445,630 B2 | 11/2008 | Lashinski |
| 7,445,632 B2 | 11/2008 | McGuckin, Jr. |
| 7,455,689 B2 | 11/2008 | Johnson |
| 7,462,156 B2 | 12/2008 | Mitrev |
| 7,462,184 B2 | 12/2008 | Worley |
| 7,462,191 B2 | 12/2008 | Spenser |
| 7,468,050 B1 | 12/2008 | Kantrowitz |
| 7,470,284 B2 | 12/2008 | Lambrecht |
| 7,470,285 B2 | 12/2008 | Nugent |
| 7,473,275 B2 | 1/2009 | Marquez |
| 7,476,196 B2 | 1/2009 | Spence |
| 7,476,199 B2 | 1/2009 | Spence |
| 7,476,200 B2 | 1/2009 | Tal |
| 7,481,838 B2 | 1/2009 | Carpentier |
| 7,485,088 B2 | 2/2009 | Murphy |
| 7,485,143 B2 | 2/2009 | Webler |
| 7,488,346 B2 | 2/2009 | Navia |
| 7,497,824 B2 | 3/2009 | Taylor |
| 7,500,949 B2 | 3/2009 | Gottlieb |
| 7,500,989 B2 | 3/2009 | Solem |
| 7,503,929 B2 | 3/2009 | Johnson |
| 7,503,930 B2 | 3/2009 | Sharkawy |
| 7,507,199 B2 | 3/2009 | Wang |
| 7,510,572 B2* | 3/2009 | Gabbay ................ 623/2.11 |
| 7,510,575 B2 | 3/2009 | Spenser |
| 7,510,577 B2 | 3/2009 | Moaddeb |
| 7,513,863 B2 | 4/2009 | Bolling |
| 7,513,909 B2 | 4/2009 | Lane |
| 7,522,950 B2 | 4/2009 | Fuimaono |
| 7,530,253 B2 | 5/2009 | Spenser |
| 7,534,261 B2 | 5/2009 | Friedman |
| 7,556,646 B2 | 7/2009 | Yang |
| 7,578,828 B2 | 8/2009 | Gittings |
| 7,585,321 B2 | 9/2009 | Cribier |
| 7,591,848 B2 | 9/2009 | Allen |
| 7,618,446 B2 | 11/2009 | Andersen et al. |
| 7,625,403 B2 | 12/2009 | Krivoruchko |
| 7,632,296 B2 | 12/2009 | Malewicz |
| 7,682,390 B2 | 3/2010 | Seguin |
| 7,780,726 B2 | 8/2010 | Seguin |
| 7,846,203 B2 | 12/2010 | Cribier |
| 7,846,204 B2 | 12/2010 | Letac et al. |
| 7,896,915 B2 | 3/2011 | Guyenot et al. |
| 7,914,575 B2 | 3/2011 | Guyenot et al. |
| 7,947,075 B2 | 5/2011 | Goetz et al. |
| 7,959,672 B2 | 6/2011 | Salahieh et al. |
| 8,002,825 B2 | 8/2011 | Letac et al. |
| 8,057,540 B2 | 11/2011 | Letac et al. |
| 8,062,749 B2 | 11/2011 | Shelestak et al. |
| 8,092,518 B2 | 1/2012 | Schreck |
| 8,092,520 B2 | 1/2012 | Quadri |
| 8,603,159 B2 | 12/2013 | Seguin et al. |
| 8,628,571 B1 | 1/2014 | Hacohen et al. |
| 8,845,721 B2 | 9/2014 | Braido et al. |
| 2002/0117789 A1 | 8/2002 | Childers et al. |
| 2003/0028213 A1 | 2/2003 | Thill et al. |
| 2003/0040792 A1 | 2/2003 | Gabbay |
| 2003/0114913 A1* | 6/2003 | Spenser et al. ............. 623/1.11 |
| 2004/0019374 A1 | 1/2004 | Hojeibane et al. |
| 2004/0044361 A1 | 3/2004 | Frazier et al. |
| 2004/0044400 A1 | 3/2004 | Cheng et al. |
| 2004/0093060 A1 | 5/2004 | Seguin et al. |
| 2004/0093063 A1* | 5/2004 | Wright et al. ............. 623/1.12 |
| 2004/0106976 A1 | 6/2004 | Bailey et al. |

(56) References Cited

U.S. PATENT DOCUMENTS

| | | |
|---|---|---|
| 2004/0210304 A1* | 10/2004 | Seguin et al. ............... 623/2.11 |
| 2004/0236411 A1* | 11/2004 | Sarac et al. ................. 623/1.26 |
| 2004/0254594 A1 | 12/2004 | Alfaro |
| 2004/0260389 A1* | 12/2004 | Case et al. .................. 623/1.24 |
| 2005/0043759 A1 | 2/2005 | Chanduszko |
| 2005/0070794 A1 | 3/2005 | Deal et al. |
| 2005/0113910 A1 | 5/2005 | Paniagua et al. |
| 2005/0137681 A1 | 6/2005 | Shoemaker et al. |
| 2005/0137688 A1 | 6/2005 | Salahieh et al. |
| 2005/0137693 A1 | 6/2005 | Haug et al. |
| 2005/0137696 A1 | 6/2005 | Salahieh et al. |
| 2005/0137702 A1 | 6/2005 | Haug et al. |
| 2005/0182483 A1 | 8/2005 | Osborne et al. |
| 2005/0222674 A1* | 10/2005 | Paine .......................... 623/1.24 |
| 2005/0267523 A1 | 12/2005 | Devellian et al. |
| 2005/0283231 A1 | 12/2005 | Haug et al. |
| 2005/0288706 A1 | 12/2005 | Widomski et al. |
| 2006/0004442 A1 | 1/2006 | Spenser et al. |
| 2006/0122692 A1 | 6/2006 | Gilad et al. |
| 2006/0161248 A1 | 7/2006 | Case et al. |
| 2006/0190070 A1* | 8/2006 | Dieck et al. ................. 623/1.12 |
| 2006/0259136 A1 | 11/2006 | Nguyen et al. |
| 2006/0265056 A1 | 11/2006 | Nguyen |
| 2006/0287717 A1 | 12/2006 | Rowe et al. |
| 2007/0060998 A1 | 3/2007 | Butterwick et al. |
| 2007/0061002 A1 | 3/2007 | Paul et al. |
| 2007/0198097 A1 | 8/2007 | Zegdi |
| 2007/0213813 A1 | 9/2007 | Von Segesser et al. |
| 2007/0239265 A1 | 10/2007 | Birdsall |
| 2007/0239269 A1 | 10/2007 | Dolan et al. |
| 2007/0244546 A1 | 10/2007 | Francis |
| 2007/0273813 A1 | 11/2007 | Yoshida et al. |
| 2007/0282436 A1 | 12/2007 | Pinchuk |
| 2008/0071361 A1 | 3/2008 | Tuval et al. |
| 2008/0071362 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0125859 A1 | 5/2008 | Salahieh et al. |
| 2008/0140189 A1 | 6/2008 | Nguyen et al. |
| 2008/0161909 A1 | 7/2008 | Kheradvar et al. |
| 2008/0177381 A1 | 7/2008 | Navia et al. |
| 2008/0195199 A1 | 8/2008 | Kheradvar et al. |
| 2008/0208327 A1 | 8/2008 | Rowe |
| 2008/0228263 A1 | 9/2008 | Ryan |
| 2008/0234814 A1 | 9/2008 | Salahieh et al. |
| 2008/0255660 A1 | 10/2008 | Guyenot et al. |
| 2008/0269878 A1 | 10/2008 | Iobbi |
| 2008/0275550 A1 | 11/2008 | Kheradvar et al. |
| 2009/0005863 A1 | 1/2009 | Goetz et al. |
| 2009/0164006 A1 | 6/2009 | Seguin et al. |
| 2009/0171432 A1 | 7/2009 | Von Segesser et al. |
| 2009/0171447 A1 | 7/2009 | Von Segesser et al. |
| 2009/0276040 A1 | 11/2009 | Rowe et al. |
| 2009/0287299 A1 | 11/2009 | Tabor et al. |
| 2010/0168839 A1 | 7/2010 | Braido et al. |
| 2011/0022157 A1 | 1/2011 | Essinger et al. |
| 2011/0040374 A1 | 2/2011 | Goetz et al. |
| 2011/0224780 A1 | 9/2011 | Tabor et al. |
| 2012/0101571 A1 | 4/2012 | Thambar et al. |
| 2012/0101572 A1 | 4/2012 | Kovalsky et al. |
| 2012/0116496 A1 | 5/2012 | Chuter et al. |
| 2012/0123529 A1 | 5/2012 | Levi et al. |
| 2012/0172982 A1 | 7/2012 | Stacchino et al. |
| 2012/0303116 A1 | 11/2012 | Gorman, Iii et al. |

FOREIGN PATENT DOCUMENTS

| | | |
|---|---|---|
| AU | 2009200985 A1 | 4/2009 |
| CA | 2634358 A1 | 6/2007 |
| CA | 2657839 A1 | 3/2008 |
| CA | 2659690 A1 | 3/2008 |
| DE | 20003874 U1 | 6/2000 |
| DE | 19857887 A1 | 7/2000 |
| DE | 102005003632 A1 | 8/2006 |
| DE | 202007005491 U1 | 7/2007 |
| EP | 0592410 B1 | 10/1995 |
| EP | 0657147 A2 | 8/1999 |
| EP | 0696447 A2 | 1/2000 |
| EP | 1262201 A1 | 12/2002 |
| EP | 1264582 A2 | 12/2002 |
| EP | 1093771 A1 | 6/2005 |
| EP | 0943302 A2 | 10/2005 |
| EP | 1267753 B1 | 10/2005 |
| EP | 1598031 A1 | 11/2005 |
| EP | 1251797 B1 | 11/2007 |
| EP | 1968491 A2 | 9/2008 |
| EP | 2033593 A1 | 3/2009 |
| EP | 2047824 A1 | 4/2009 |
| EP | 2059192 A1 | 5/2009 |
| EP | 2074964 A1 | 7/2009 |
| EP | 1968491 | 7/2010 |
| EP | 2059192 | 7/2011 |
| FR | 2874812 A1 | 3/2006 |
| WO | 98/29057 A1 | 7/1998 |
| WO | 00/28922 A1 | 5/2000 |
| WO | 2000047139 A1 | 8/2000 |
| WO | 20001053122 A1 | 9/2000 |
| WO | 01/49213 A2 | 7/2001 |
| WO | 01/62189 A1 | 8/2001 |
| WO | 02/067782 A2 | 9/2002 |
| WO | 02/076349 A1 | 10/2002 |
| WO | 03/047468 A1 | 6/2003 |
| WO | 03/063729 A2 | 11/2003 |
| WO | 03/003949 A2 | 1/2004 |
| WO | WO 2004019825 A1 * | 3/2004 ............... A61F 2/24 |
| WO | 2005/07343 A1 | 8/2005 |
| WO | 2005102015 A2 | 11/2005 |
| WO | 2006068944 A2 | 6/2006 |
| WO | WO-2006058163 A2 | 6/2006 |
| WO | WO-2006076890 A1 | 7/2006 |
| WO | WO-2006086135 A2 | 8/2006 |
| WO | 2006127765 A1 | 11/2006 |
| WO | 2007/071436 A2 | 6/2007 |
| WO | 2006083763 A2 | 8/2007 |
| WO | 2008/028569 A1 | 3/2008 |
| WO | 2008040555 A2 | 4/2008 |
| WO | 2008070442 A1 | 6/2008 |
| WO | 2009024859 A2 | 2/2009 |
| WO | 2009053497 A1 | 4/2009 |
| WO | 2010049160 A1 | 5/2009 |
| WO | 2009091509 A1 | 7/2009 |
| WO | 2010045297 A2 | 4/2010 |
| WO | 2010083558 A1 | 7/2010 |
| WO | 2010045238 A2 | 10/2010 |
| WO | 2011051043 A1 | 5/2011 |
| WO | 2011057087 A1 | 5/2011 |
| WO | 2013033791 A1 | 3/2013 |
| WO | 2013134214 A1 | 9/2013 |
| WO | 2014072439 A9 | 7/2014 |

OTHER PUBLICATIONS

Australian Examination Report, Application No. Au 2009200985, Date: Mar. 4, 2010.
European Examination Report, Application No. EP06841127.1, Mail Date: Feb. 6, 2009.
European Examination Report, Application No. EP07818037.9, Date: Aug. 11, 2009.
European Search Report, Application No. EP09154935.2, Date: May 29, 2009.
International Preliminary Report on Patentability, Application No. PCT/EP2006/012455, Date of Issue: Jun. 24, 2008.
International Preliminary Report on Patentability, Application No. PCT/EP2007/07413, Date of Issuance: Mar. 10, 2009.
International Search Report, Application No. PCT/EP2006/012455, Date of Mailing: Sep. 27, 2007.
Akins et al., "Risk of Reoperative Valve Replacement for Failed Mitral and Aortic Bioprostheses", Ann Thorac Surg (1998), 65:1545-52.
Ma et al., "Double-crowned valved stents for off-pump mitrel valve replacement", European Journal of Cardio-Thoracic Surgery (2005), 28:194-199.

(56) References Cited

OTHER PUBLICATIONS

Pawelec-Wojtalk, "Closure of left ventricle perforation with the use of muscular VSD occluder", European Journal of Cardio-Thoracic Surgery (2005), 27:714-716.
Weerasinghe et al., "First Redo Heart Valve Replacement: A 10-Year Analysis", Circulation (1999), 99:655-658.
Dewey et al., "Transapical aortic valve implantation: an animal feasibility study", The annals of thoracic surgery, (2006): 82:110-116.
Mack, M.J., "Minimally invasive cardiac surgery", Surg Endosc, (2006) 20:S488-S492.
Walther et al., "Transapical approach for sutureless stent-fixed aortic valve implantation: experimental results", European Journal of Cardiao-thoriacic Surgery 29 (2006), 703-708.
International Search Report for International Application No. PCT/EP2008/064558, date of completion of report, Mar. 18, 2009 and Written Opinion of the International Search Authority for International Application No. PCT/EP20081064558.
Partial International Search Report for International Application No. PCT/EP2014/055044, filed Mar. 13, 2014.
ISR & WO for PCT/IB2008/002180, mailed Apr. 15, 2009.
IRPR for PCT/IB2008/002180, issued Feb. 24, 2010.
ISR for PCT/EP2010/057798, mailed Sep. 12, 2010.
IRPR for PCT/EP20101057798, mailed Dec. 6, 2011.
ISR for PCT/EP2007/007413, mailed Jan. 28, 2008.
IPRP for PCT/EP2007/007413, issued Mar. 10, 2009.
IPRP issued May 8, 2012 for PCT/EP2010/063306.
ISR mailed Feb. 17, 2012 for PCT/EP2011/066677.
IPRP issued Mar. 26, 2013 for PCT/EP2011/066677.
ISR mailed Apr. 17, 2014 for PCT/EP2013/073318.

* cited by examiner

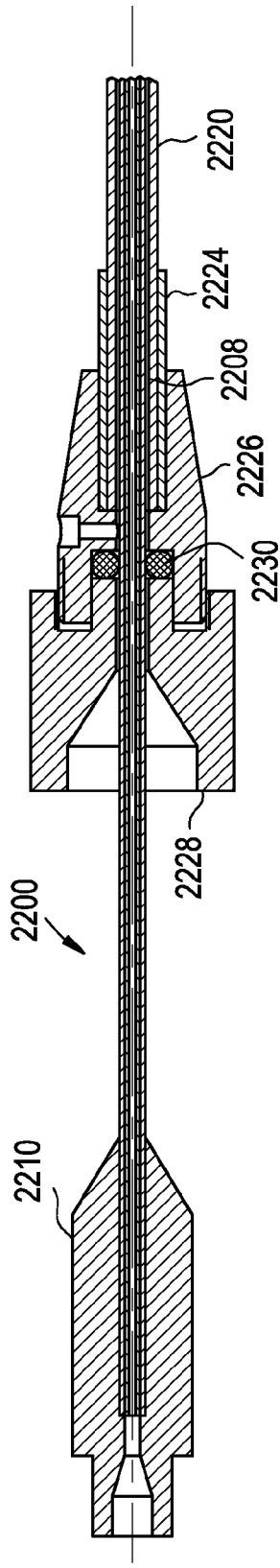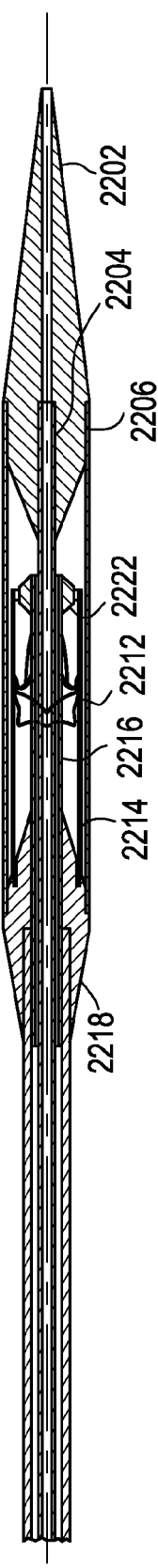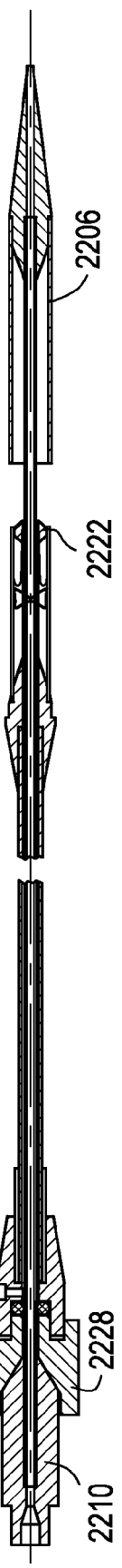

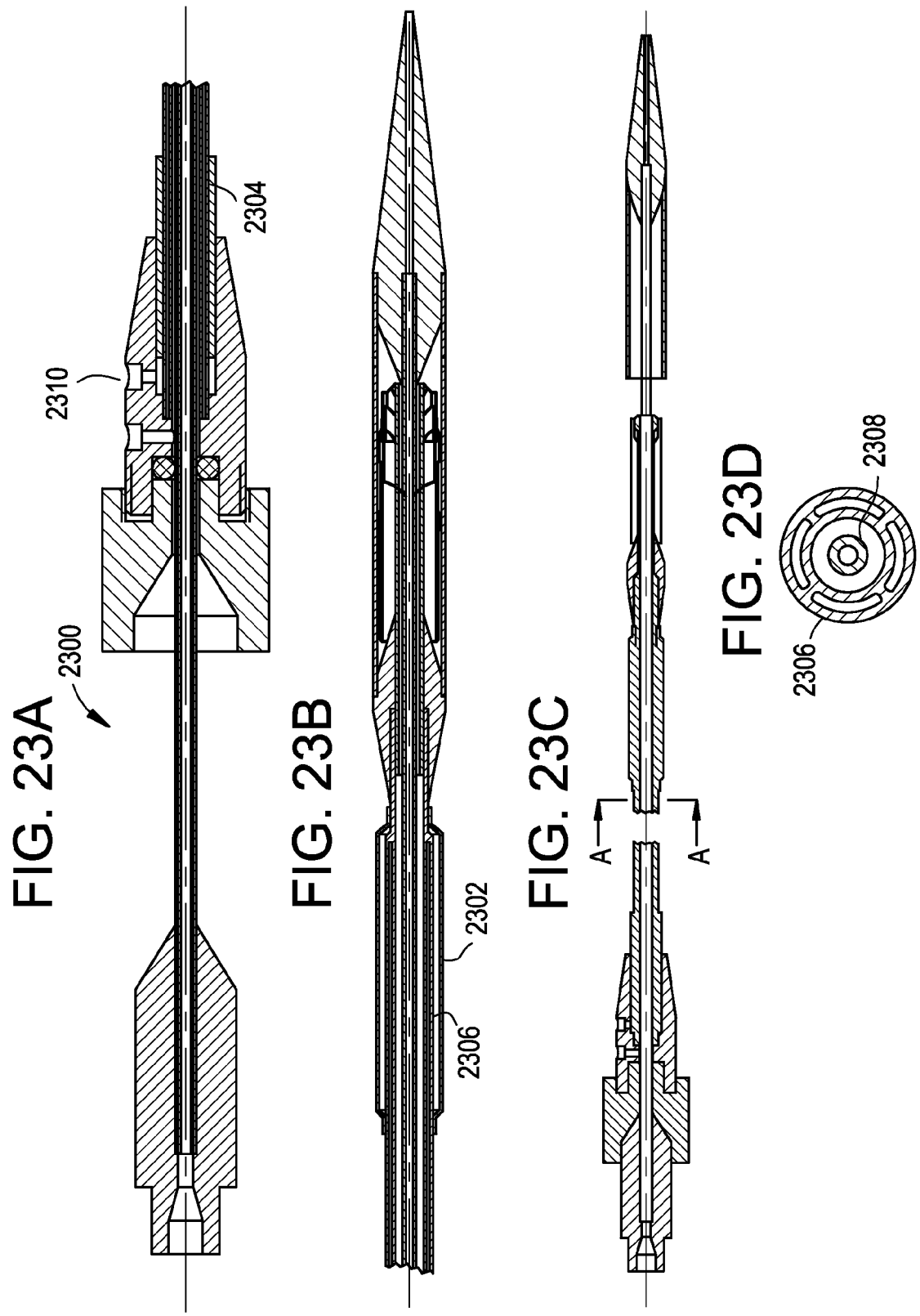

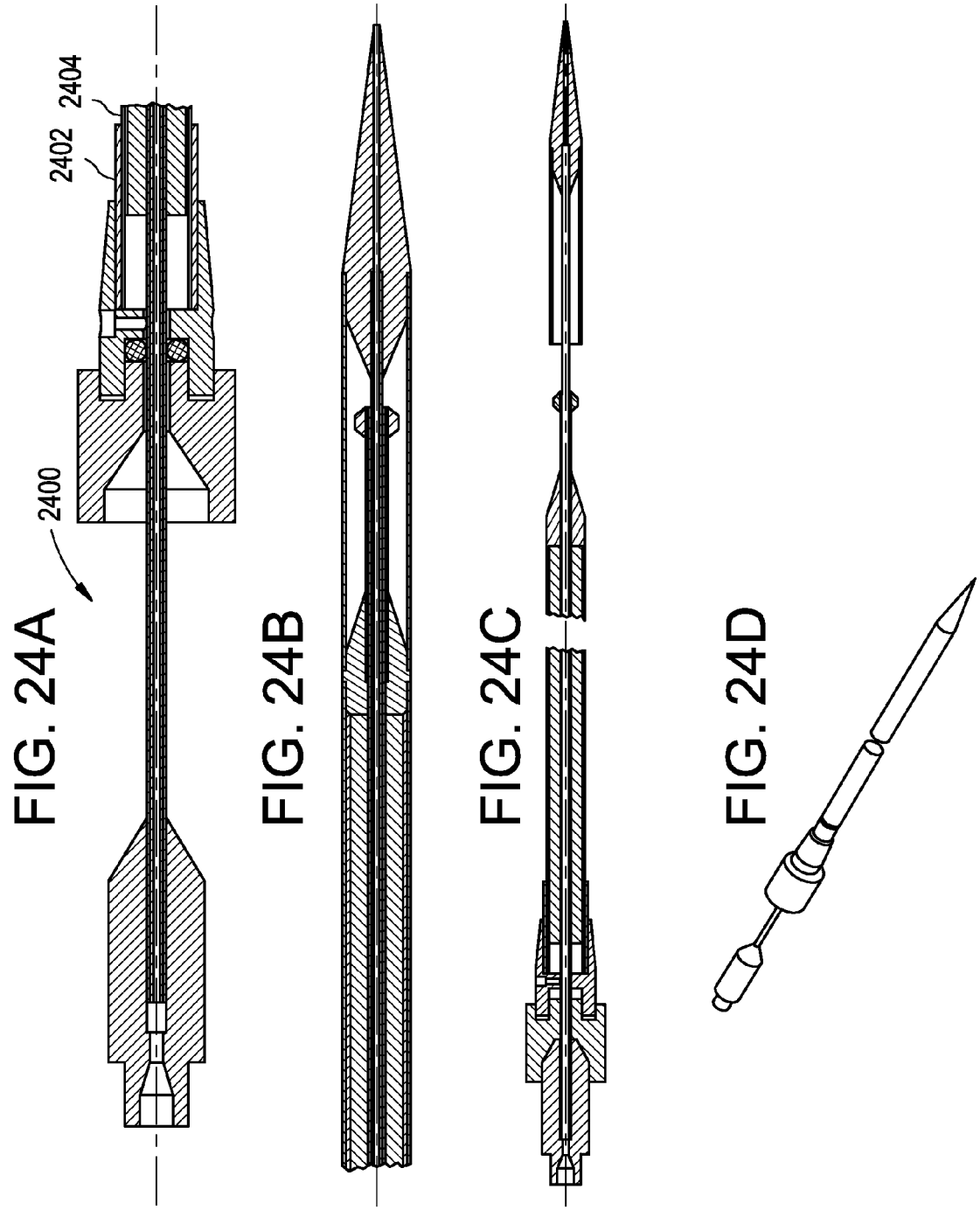

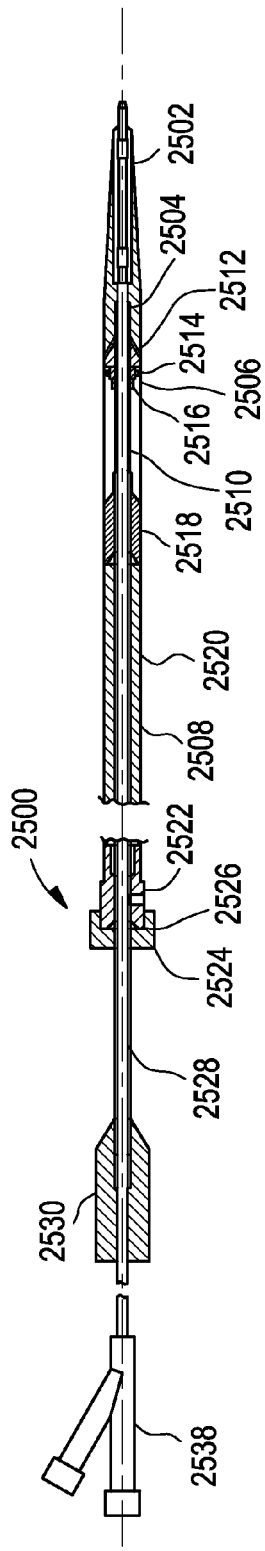
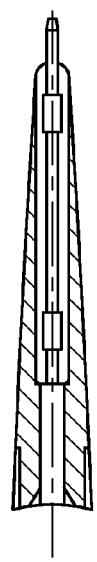
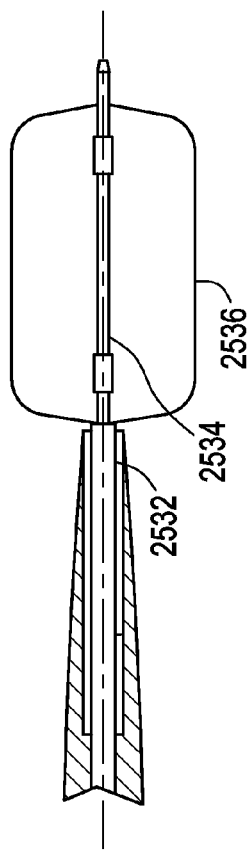
FIG. 25A
FIG. 25B
FIG. 25C

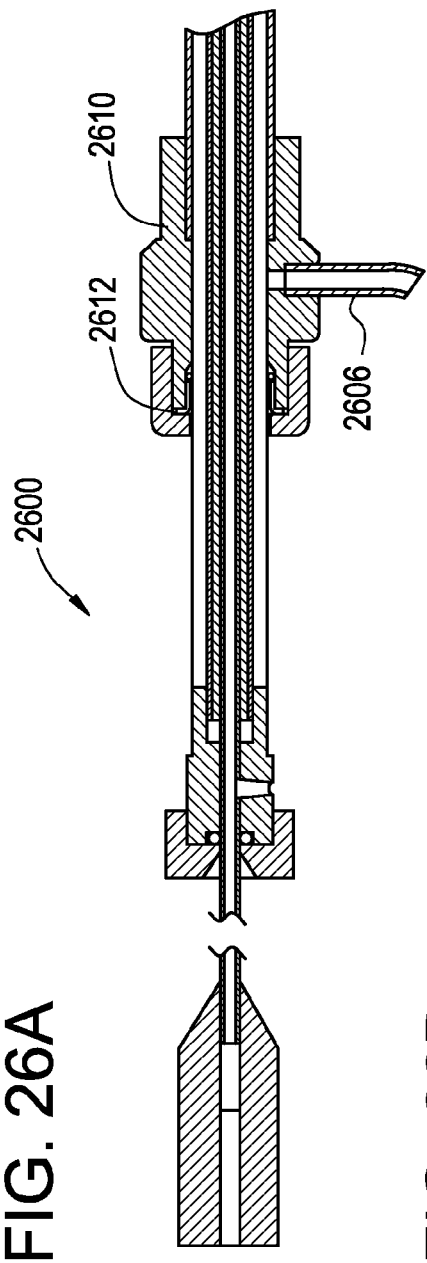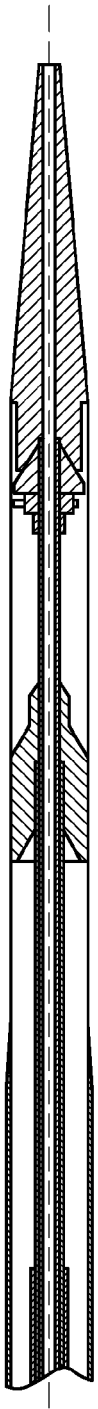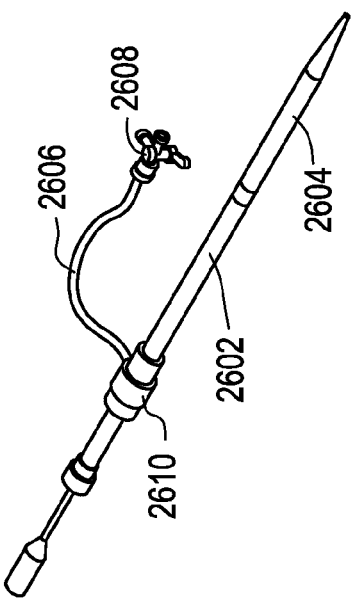
FIG. 26A
FIG. 26B
FIG. 26C

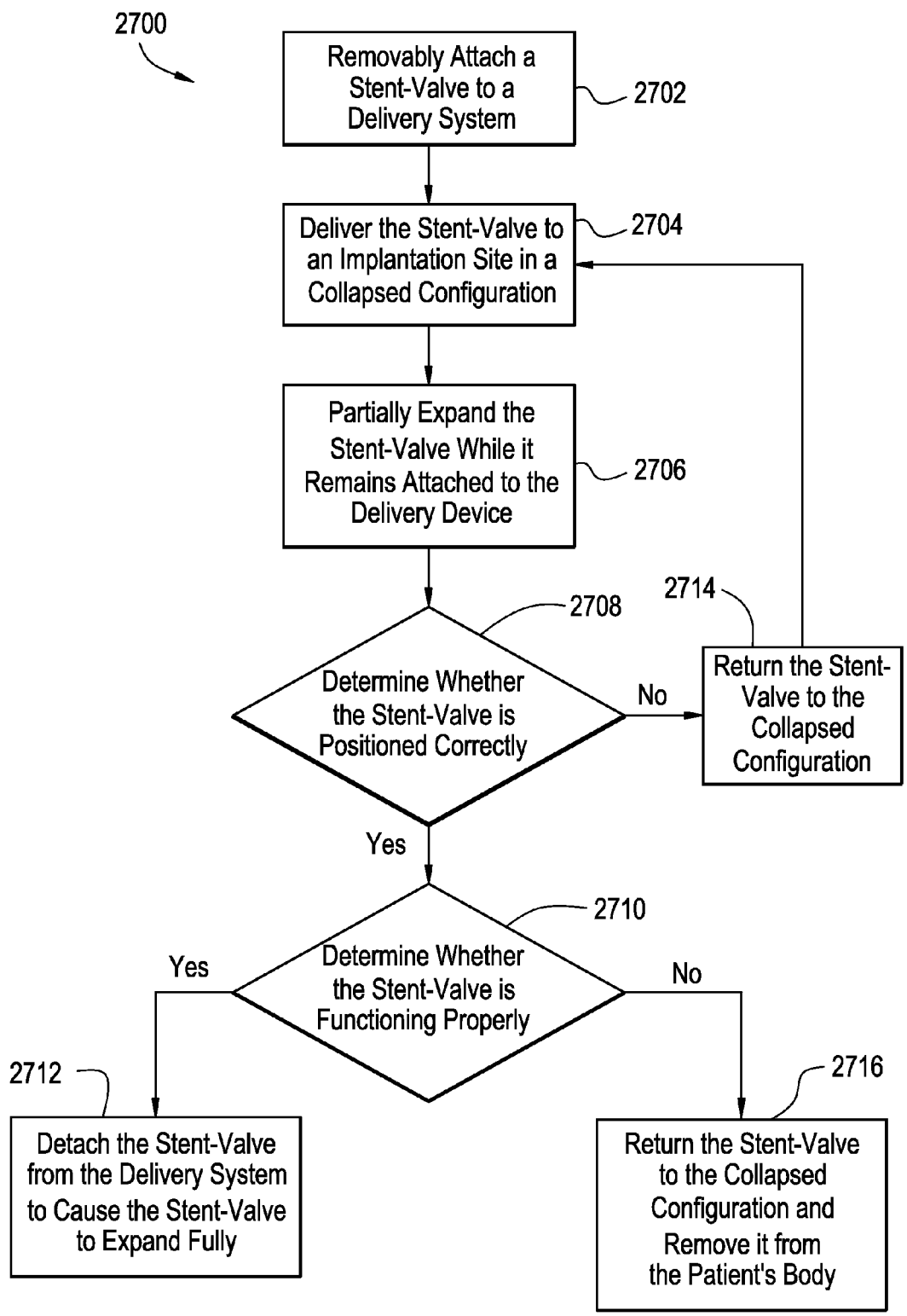

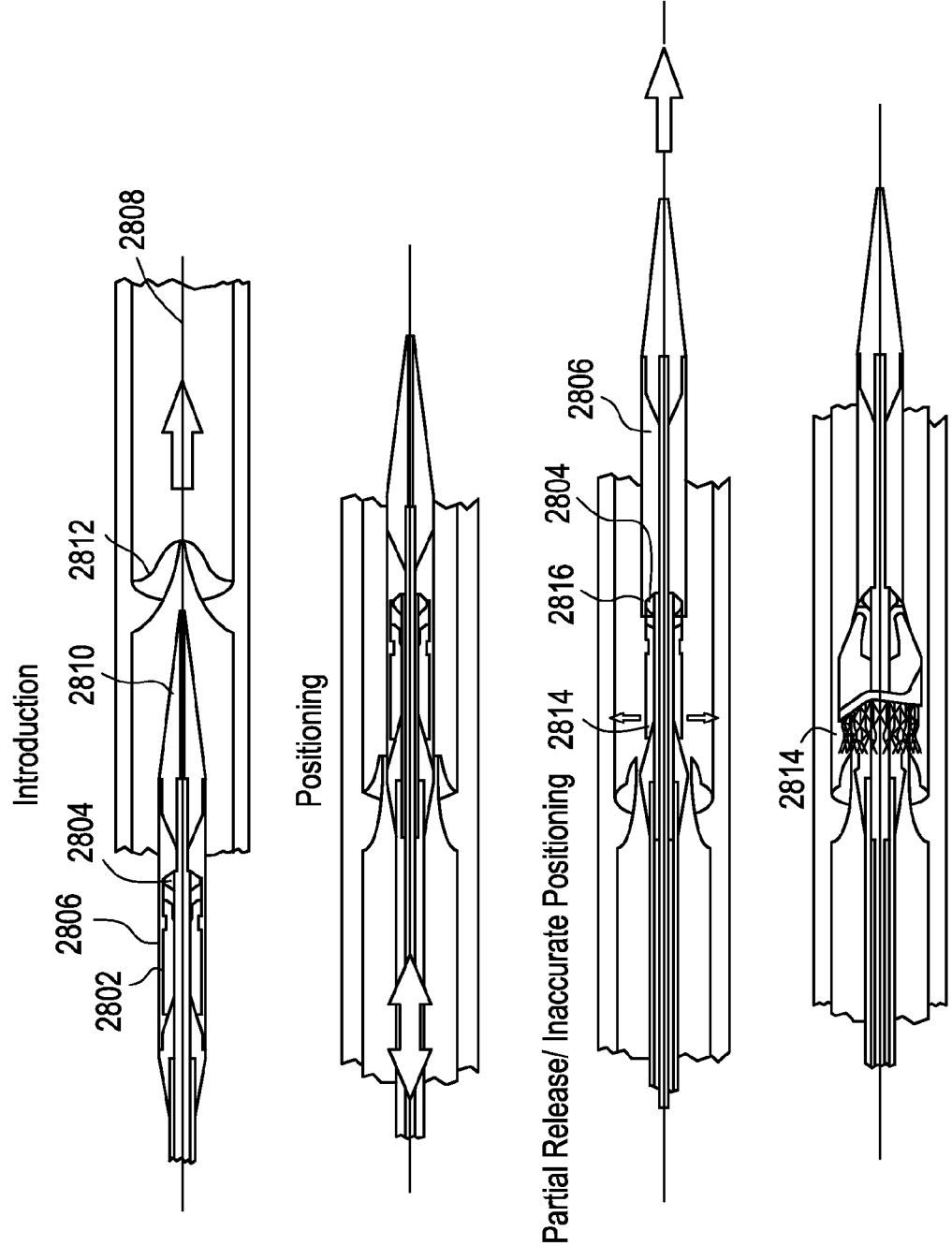

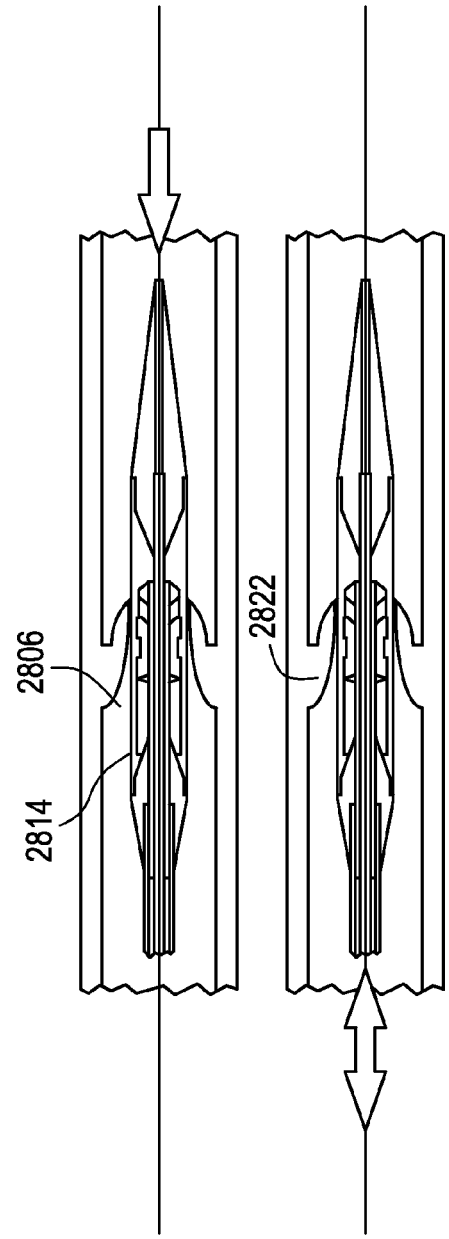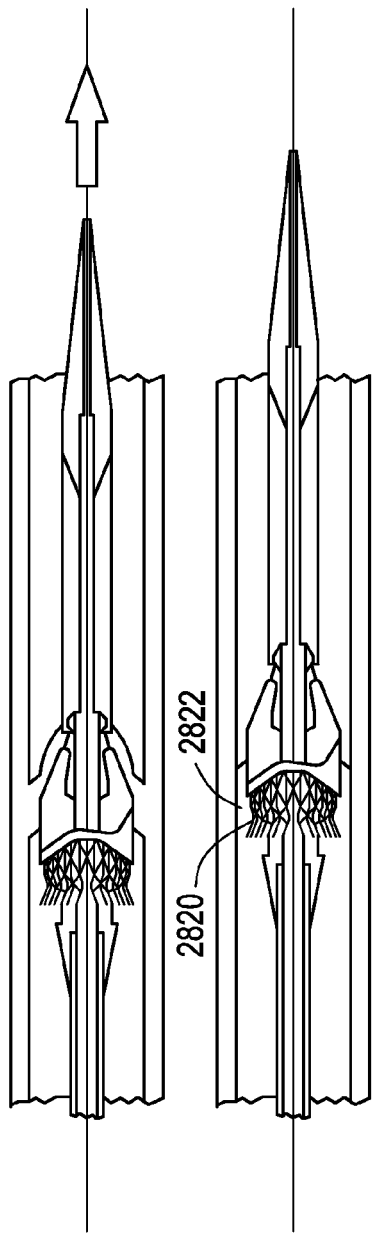

3000

3100

FIG. 32A
FIG. 32B
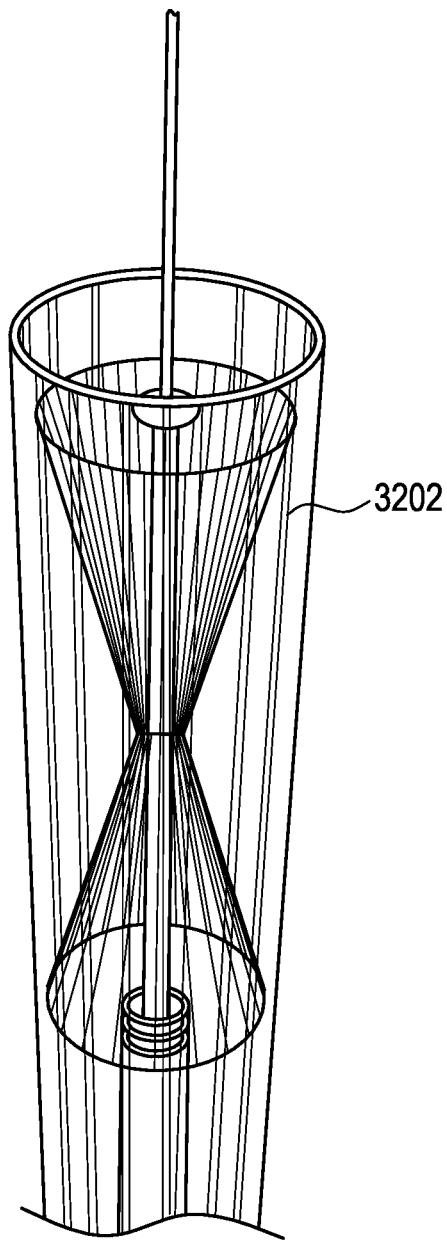
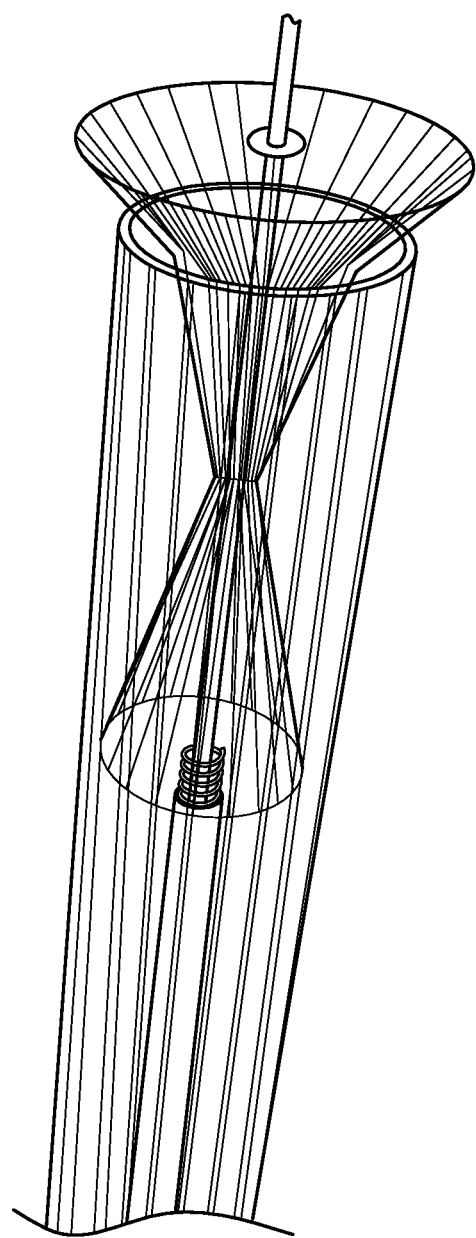
3202

STENT-VALVES FOR VALVE REPLACEMENT AND ASSOCIATED METHODS AND SYSTEMS FOR SURGERY

CROSS-REFERENCE TO RELATED APPLICATIONS

The present application is a divisional of U.S. patent application Ser. No. 11/700,922, filed Dec. 21, 2006, now abandoned, which claims the benefit of U.S. Provisional Patent Application Nos. 60/753,071, filed Dec. 22, 2005, 60/755,590, filed Dec. 29, 2005, and 60/843,181, filed Sep. 7, 2006, each of which is incorporated by reference herein in its entirety.

FIELD OF THE INVENTION

Embodiments of the present invention relate to stent-valves, associated methods and systems for their delivery via minimally-invasive surgery, and guide-wire compatible closure devices for sealing access orifices.

BACKGROUND OF THE INVENTION

Conventional approaches for cardiac valve replacement require the cutting of a relatively large opening in the patient's sternum ("sternotomy") or thoracic cavity ("thoracotomy") in order to allow the surgeon to access the patient's heart. Additionally, these approaches require arrest of the patient's heart and a cardiopulmonary bypass (i.e., use of a heart-lung bypass machine to oxygenate and circulate the patient's blood). Despite their invasiveness, these surgical approaches may be reasonably safe for a first intervention. However, tissue adherences resulting from the first surgery may increase the risks (e.g., death) associated with subsequent valve replacement surgeries. See Akins et al., "Risk of Reoperative Valve Replacement for Failed Mitral and Aortic Bioprostheses", Ann Thorac Surg 1998; 65:1545-52; and Weerasinghe et al., "First Redo Heart Valve Replacement—A 10-Year Analysis", Circulation 1999; 99:655-658; each of which is incorporated by reference herein in its entirety.

Synthetic valves and biological valves have been used for cardiac valve replacement with varying results. Synthetic valves rarely fail but require life-long anti-coagulant treatment to prevent blood from clotting (thrombosis) in and around the replacement valve. Such anti-coagulant treatment significantly limits patients' activities and can cause various other complications. Biological valves do not require such anti-coagulation treatment but typically fail within 10-15 years. Thus, to limit the need for and risks associated with re-operation on failed biological valves, traditionally only patients with less than about 10-15 years to live have received biological valve replacements. Patients with longer life expectancies have received synthetic valves and anti-coagulant treatment.

Attempts have been made to develop less-invasive surgical methods for cardiac valve replacement. These surgical methods, referred to as percutaneous heart valve replacement therapies (PHVT), use a catheter to deliver a replacement valve to an implantation site using the patient's vascular system. These PHVT attempts have various shortcomings, including their inability to ensure proper positioning and stability of the replacement valve within the patient's body.

Conventional closure devices for closing access orifices are also lacking in several respects, including the looseness of their fit which can cause bleeding after surgery. These closure devices also lack a central lumen, which renders them incompatible with guide wire delivery systems. One such conventional closure device is described in Malgorzata Pawelec-Wojtalik, "Closure of left ventricle perforation with the use of muscular VSD occluder", European Journal of Cardio-Thoracic Surgery 27 (2005) 714-716, which is incorporated by reference herein in its entirety.

In view of the foregoing, it would be desirable to provide improved methods, systems, and devices for cardiac valve replacement.

SUMMARY OF THE INVENTION

Some embodiments of the present invention are directed to systems, methods, and devices for cardiac valve replacement. For example, these methods, systems, and devices may be applicable to the full range of cardiac-valve therapies including the replacement of failed aortic, mitral, tricuspid, and pulmonary valves. In some embodiments, the present invention may facilitate a surgical approach whereby surgery is performed on a beating heart without the need for an open-chest cavity and heart-lung bypass. This minimally-invasive surgical approach may reduce the risks associated with replacing a failed native valve in the first instance, as well as the risks associated with secondary or subsequent surgeries to replace failed artificial (e.g., biological or synthetic) valves.

Stent-valves according to some embodiments of the present invention may include a valve component and at least one stent component. The valve component may include a biological or synthetic (e.g., mechanical) valve and/or any other suitable material(s). The stent component may include a first section (e.g., proximal section), a second section configured to house the valve component, and a third section (e.g., distal section). The stent and valve components may be capable of at least two configurations: a collapsed configuration (e.g., during delivery) and an expanded configuration (e.g., after implantation).

In some embodiments, the first section of the stent valve may include a fixation element. Such a fixation element may include, for example, an annular groove for securing the stent-valve in place at an implantation site. When the stent-valve includes a single stent ("single-stent-valve"), the annular groove may be configured to receive the annulus of the valve in need of replacement. When the stent-valve includes two stents ("double-stent-valve"), the annular groove of the first stent component may be configured for matable attachment to a complimentary annular projection of a second stent component (i.e., a positioning stent). In turn, the second stent component may be anchored at the implantation site, for example, to the valve in need of replacement and/or adjoining structures.

Alternatively or additionally, in some embodiments the third section of the stent component may include at least one attachment element. Each attachment element of the stent-valve may include, for example, a geometrical opening (e.g., circular or ovular), hook, or strap configured for removable attachment to a complimentary structure of a delivery device. In addition, each attachment element may correspond to all or a portion of a commissural post, to which a commissure between two valve leaflets may be attached. The attachment element(s) may allow the stent-valve to be partially expanded within a patient's body while the stent-valve remains attached to the delivery device. This may allow the stent-valve to be returned to a collapsed configuration and repositioned within the patient's body when it is determined that fully expanding the stent-valve would cause the stent-valve to be installed incorrectly. Alternatively or additionally, this may allow the stent-valve to be returned to the collapsed configuration and removed from the patient's body when it is determined that the stent-valve is not functioning properly (e.g., not permitting sufficient flow). In some embodiments, the stent-valve may include one attachment element. In other embodiments, the stent-valve may include at least two, three, six, or any other suitable number of attachment elements. In some embodiments, the fully-expanded stent diameter in the region of the attachment element(s) may be smaller than the diameter of the region that houses an associated valve. This may reduce the risk of injury to the patient's body (e.g., perforation of the aorta) from the attachment elements and/or make it easier to affix the attachment elements to the complimentary structure of the delivery device.

In some embodiments, the stent component of the stent-valve may include a lattice structure with a plurality of cells. The lattice structure may be formed from, for example, a shape-memory alloy such as nitinol or any other suitable material(s). The cells in the lattice structure may be most densely populated in the section of the stent component that includes the fixation element. This may provide added support to the fixation element and increase the stability of the stent-valve. In some embodiments, the lattice structure may form at least one elongate stem (e.g., commissural post) that extends distally along the stent component towards the at least one attachment element. The at least one stem may connect directly to the at least one attachment element. Alternatively, the lattice structure may form at least one supporting element for connecting the at least one stem to the at least one attachment element. In some embodiments, all of the cells in the lattice structure may be closed cells, which may facilitate recapture of the stent-valve from the partially-expanded configuration to the collapsed configuration.

Still other embodiments of the present invention are directed to a method for replacing a valve. A stent-valve is provided that includes a stent component with an annular groove, and the stent-valve is secured axially to an annulus of the valve in need of replacement. In some embodiments, providing a stent-valve may include suturing a valve component to the stent component. Alternatively or additionally, providing a stent-valve may include expanding a valve component within the stent component in order to form a friction fitting. In some embodiments, providing a stent-valve may include securing a valve component to the stent component with a hook-and-loop (e.g., VELCRO®) fastening system.

In other embodiments of the present invention, a method for replacing a valve is provided whereby a first stent component that includes an annular element is implanted such that at least a portion of the first stent component is housed within a valve in need of replacement. A stent-valve that includes a second stent component is positioned within the first stent component by matably attaching a complimentary annular element of the second stent component to the annular element of the first stent component.

In still other embodiments of the present invention, a stent-valve delivery system is provided. A first assembly is provided that includes an outer sheath and a guide wire tubing. The delivery system also includes a second assembly including a stent holder configured for removable attachment to at least one attachment element of a stent-valve. The stent-valve may be positioned over the guide wire of the first assembly. The first assembly and the second assembly may be configured for relative movement with respect to one another in order to transition from a closed position to an open position. In the closed position, the outer sheath may encompass the stent-valve still attached to the stent holder and thus constrain expansion of the stent-valve. In the open position, the outer sheath may not constrain expansion of the stent-valve and thus the stent-valve may detach from the stent holder and expand to a fully expanded configuration.

In some embodiments, the first assembly and the second assembly may be configured to transition from the closed position, to a partially-open position, to the open position. In the partially-open position, the stent-valve may expand partially but not detach from the stent holder because the outer sheath may still encompass the at least one attachment element of the stent-valve and the stent holder. When the stent-valve is in the partially-expanded configuration, it may be determined whether the stent-valve will be positioned correctly if the stent-valve is expanded to the fully expanded configuration. Alternatively or additionally, the functionality of the stent-valve may be tested (e.g., to determine whether the stent-valve will permit sufficient blood-flow) when the stent-valve is in the partially-expanded configuration.

In some embodiments, the stent-valve delivery system may include at least one balloon (e.g., proximal to the stent-valve or other stent to be delivered) configured to cause expansion of the stent-valve or positioning stent upon inflation of the at least one balloon.

In some embodiments, the stent-valve delivery system may include a push handle that causes the relative movement of the first assembly and the second assembly. Alternatively, the stent-valve delivery system may include a screw mechanism for translating rotational movement of a handle into the relative movement of the first assembly and the second assembly.

In some embodiments, the stent-valve delivery system may include an integrated introducer within which the first assembly and the second assembly are positioned during delivery of the stent-valve to an implantation site. The integrated introducer may be configured to remain within a patient's body even after the first assembly and the second assembly are removed, for example, to allow for the introduction of an occluder.

In some embodiments, after expansion of the stent-valve to the fully expanded configuration, the delivery system may be configured to return to the closed position by passing the second assembly through the stent-valve towards a distal end of the first assembly.

Still other embodiments of the present invention are directed to a method for delivering a stent-valve to an implantation site whereby the stent-valve is removably attached to a delivery device and the stent-valve is delivered to the implantation site in a collapsed configuration. The stent-valve may be partially expanded while maintaining the stent-valve attached to the delivery device. A determination with respect to the stent-valve may be made when the stent-valve is in the partially-expanded configuration. When the determination yields a positive response, the stent-valve may be expanded to its fully expanded configuration by causing the stent-valve to detach from the delivery device.

In one particular embodiment, it may be determined whether the stent-valve is positioned correctly at the implantation site. The stent-valve may be returned to the collapsed configuration and repositioned when the stent-valve is not positioned correctly at the implantation site.

Alternatively or additionally, it may be determined whether a valve component of the stent-valve is functioning properly, for example, by testing whether the valve component will permit sufficient blood-flow. The stent-valve may be returned to the collapsed configuration and removed from a patient's body when the stent-valve is not functioning properly.

In some embodiments, delivering the stent-valve to the implantation site may include delivering the stent-valve to the heart for replacement of a cardiac valve. The delivery may include accessing a patient's body through an intercostal space (e.g., fifth intercostal space) and penetrating the left ventricle at the apex of the heart.

In still other embodiments of the present invention, an occluder for sealing an orifice in tissue is provided. The occluder may include a first portion capable of expansion from a collapsed configuration on a luminal side of the orifice to an expanded configuration. The occluder also includes a second portion capable of expansion from a collapsed configuration to an expanded configuration on a side of the orifice opposite to the luminal side. The first portion and the second portion may form a central, hollow channel for housing a guide wire.

In some embodiments, the occluder may include a connector for connecting the occluder to a catheter. For example, the connector may include a hollow screw mechanism for connecting to a threaded catheter. The occluder may be housed by a second catheter for delivery to the tissue orifice.

In some embodiments, the top portion of the occluder may include a channel sealing mechanism for preventing blood-flow from the luminal side of the tissue orifice. For example, the channel sealing mechanism may include a membrane, foam, and/or a valve. Suitable examples of foam and/or membranous materials include polyurethane and gelatin.

In some embodiments, the top portion of the occluder may include a first material and the bottom portion of the occluder may include a second material, where the second material may be coarser than the first material. This may facilitate the formation of scar tissue on the outer portion and speed the heeling process. For example, the first and/or second materials may include felt(s) and/or velour(s) made from Teflon, Dacron, polyurethane, polydioxanone, polyhydroxybutyrate, and/or other material.

In other embodiments of the present invention, a method for sealing an orifice in tissue is provided whereby an expandable and collapsible occlusion device is connected to a first catheter. The occlusion device may be inserted into a second catheter in a collapsed condition. The first catheter and a central channel of the occlusion device may receive a guide wire. The second catheter may be positioned in the orifice, such that a first end of the second catheter is positioned on a luminal side of the orifice. Relative-movement between the collapsed occlusion device and the second catheter may be caused in order to move the occlusion device out of the second catheter. Upon the occlusion device emerging from the first end of the second catheter, a first portion of the occlusion device may expand on the luminal side of the orifice. Upon the occlusion device being completely emerged from the second catheter, a second portion of the occlusion device may expand.

BRIEF DESCRIPTION OF THE DRAWINGS

For a better understanding of the present invention, reference is made to the following description, taken in conjunction with the accompanying drawings, in which like reference characters refer to like parts throughout, and in which:

FIGS. 22A-22D show a delivery system for delivering a self-expanding stent-valve to an implantation site according to some embodiments of the present invention;

FIGS. 23A-23D show a delivery system with inflatable balloon(s) according to some embodiments of the present invention;

FIGS. 24A-24D show a delivery system having a proximal outer shaft with an increased diameter according to some embodiments of the present invention;

FIGS. 25A-25C show a delivery system with inflatable balloon(s) according to some embodiments of the present invention;

FIGS. 26A-26C show a delivery system with an integrated introducer according to some embodiments of the present invention;

FIG. 27 is a flowchart of illustrative stages involved in replacing a failed native or artificial valve according to some embodiments of the present invention;

FIGS. 28A-C illustrate the replacement of a failed valve through the use of a delivery system according to some embodiments of the present invention;

FIGS. 32A and 32B show a delivery system for an occluder according to some embodiments of the present invention.

DETAILED DESCRIPTION OF THE INVENTION

Figure 1A:
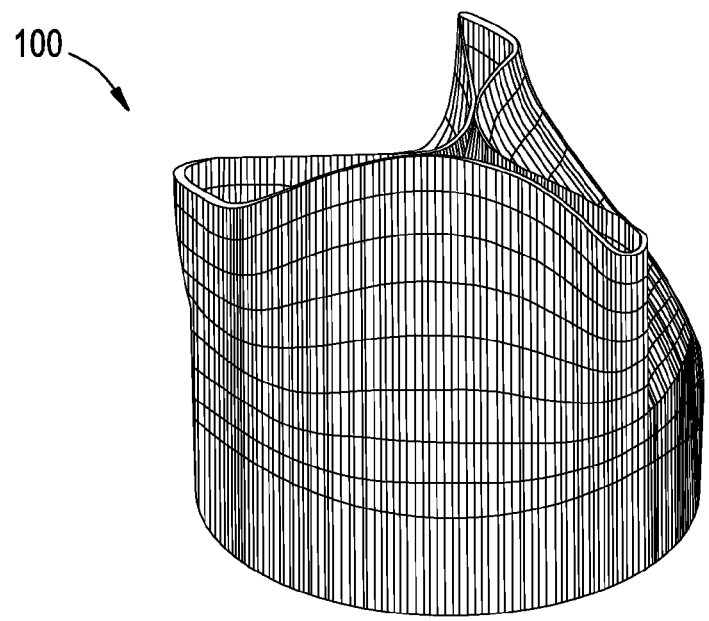
FIG. 1A shows a valve component in an expanded configuration according to some embodiments of the present invention.
Figure 1B:
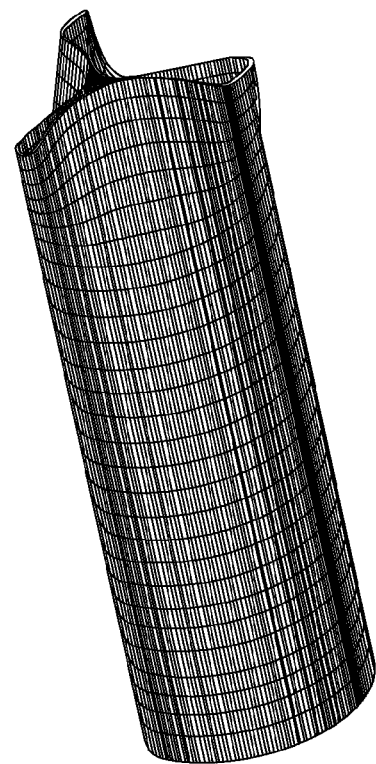
FIG. 1B shows a valve component in a collapsed configuration according to some embodiments of the present invention.
Figure 2A:
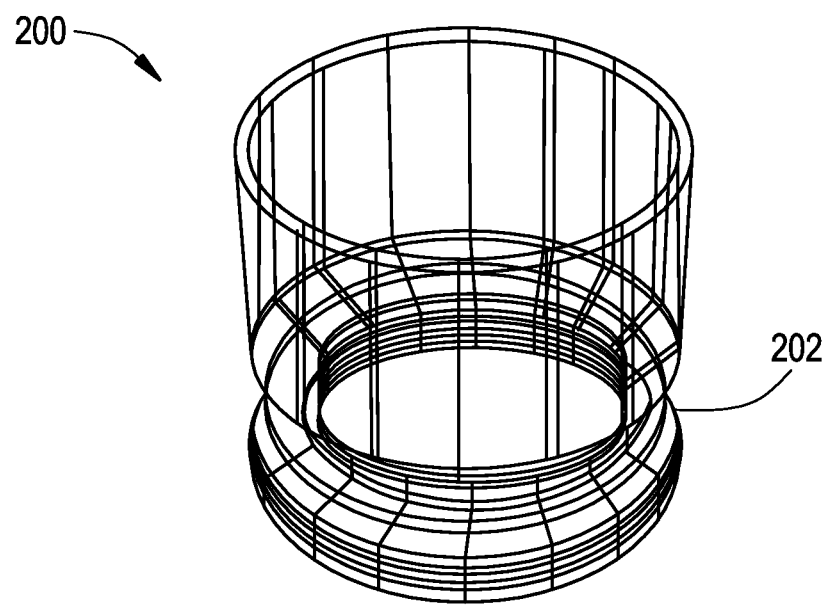
FIG. 2A shows a stent component in an expanded configuration according to some embodiments of the present invention.
Figure 2B:
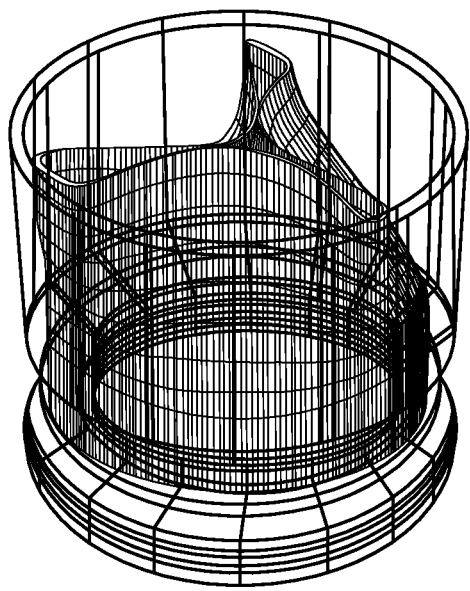
FIG. 2B shows a single-stent-valve, that includes a stent component and a valve component, in an expanded configuration according to some embodiments of the present invention.
Figure 2C:
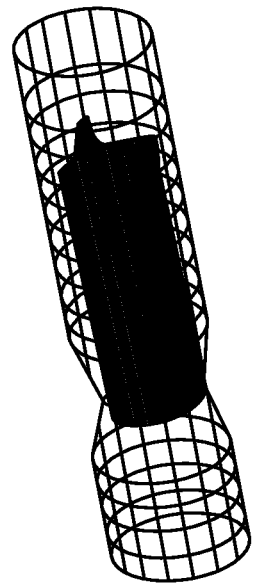
FIG. 2C shows a single-stent-valve a collapsed configuration according to some embodiments of the present invention.
Figure 3A:
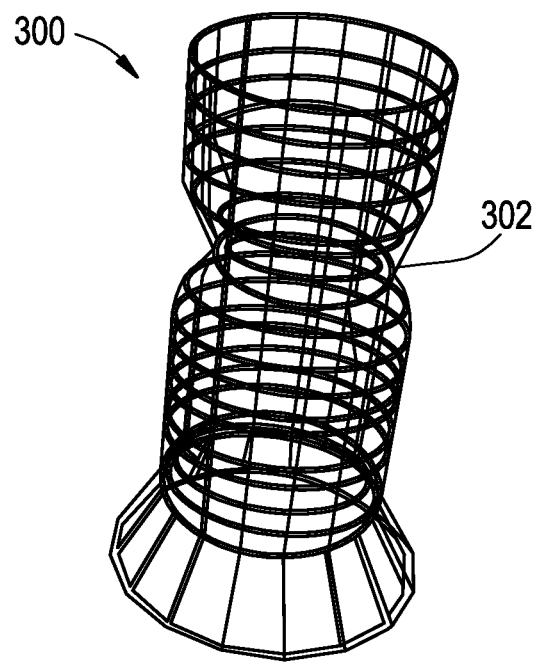
FIG. 3A shows a stent component in an expanded configuration according to some embodiments of the present invention.
Figure 3B:
FIG. 3B shows a stent component in a collapsed configuration according to some embodiments of the present invention.

FIGS. 1A-3B show components 100, 200, and 300 for use in replacing, for example, a failed (e.g., degenerated) aortic valve, mitral valve, or pulmonary cardiac valve (e.g., in a pediatric patient) in accordance with some embodiments of the present invention. More particularly, FIGS. 1A and 1B show a valve component 100. FIGS. 2A-2C show a stent component 200 for housing valve component 100. FIGS. 3A and 3B show a stent component 300 for housing stent component 200 and valve component 100. A device that includes components 100 and 200 may be referred to as a single-stent-valve. A device that additionally includes component 300 may be referred to as a double-stent-valve.

Figure 4:
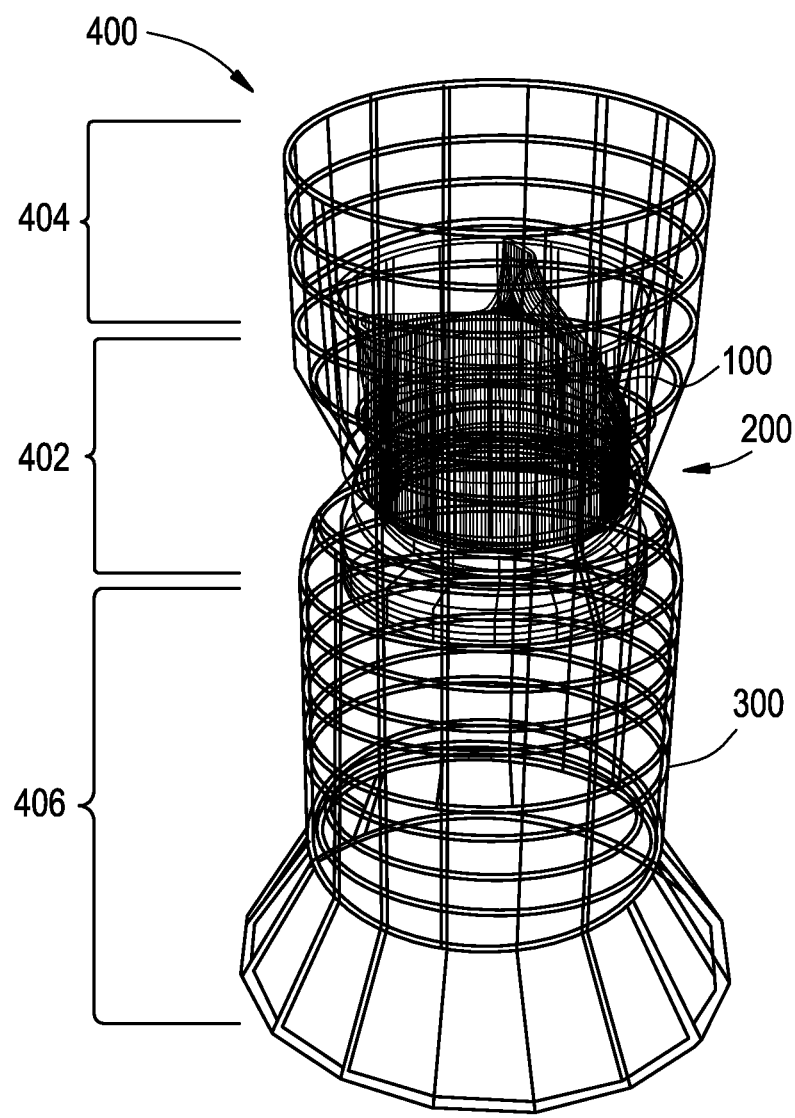
FIG. 4 shows a double-stent-valve, that includes two stent components and a valve component, in an expanded configuration according to some embodiments of the present invention.

FIG. 4 shows a double-stent-valve 400 that includes valve component 100, stent component 200, and stent component 300 in accordance with some embodiments of the present invention. Double-stent-valve 400 may replace a failed native or artificial valve. As used herein, a "native valve" refers to a valve naturally present within a patient's body. A failed native valve may be, for example, a stenotic valve. An "artificial valve" refers to a biological or synthetic (e.g., mechanical) valve introduced into the patient's body through surgery. The implantation site for a device 400 (or other replacement valve) typically includes at least a part of the area within the failed valve and/or along at least a portion of adjacent structure(s). For example, to replace a failed aortic valve, device 400 may be implanted within the patient's body such that portion 402 of the device is positioned substantially entirely within the failed aortic valve. Portion 404 of device 400 may extend along at least a portion of the aorta. Portion 406 of device 400 may extend into at least a portion of the left ventricle of the patient's heart.

Double-stent-valve 400 may be delivered to the implantation site using any suitable delivery approach. In some embodiments of the present invention, device 400 may be substantially entirely assembled from components 100, 200, and 300 outside the patient's body before device 400 is delivered to the implantation site. In other embodiments of the present invention, components 100, 200 and 300 of device 400 may be delivered to the implantation site separately in multiple steps. For example, stent component 300 may be delivered and installed at the implantation site, followed by the delivery and installation of stent component 200 and valve component 100 in one or more separate steps. In one embodiment, components 100 and 200 may be assembled outside the patient's body and then delivered and installed within component 300 at the same time. In another embodiment, stent component 200 may be delivered and installed within stent component 300, followed by the delivery and installation of valve component 100 in a separate step. Additional embodiments of double-stent-valves are described in connection with FIGS. 17-20.

In some embodiments of the present invention, a single-stent-valve (FIG. 2B) that includes valve component 100 and stent component 200 (but not stent component 300) may be used to replace a failed native or artificial valve. For example, in one particular embodiment, the single-stent-valve may replace a failed biological valve introduced to a patient's body during a prior valve replacement surgery. Thus, the surgery involving the single-stent-valve shown in FIG. 2B may be a secondary or subsequent valve replacement surgery. Although in this embodiment no new stent component 300 may be introduced to the patient's body, the single-stent-valve including components 100 and 200 may be housed by a stent and/or valve remaining at the implantation site from the prior valve replacement surgery. In some embodiments, at least a portion of the stent and/or valve from the prior surgery may be removed before the single-stent-valve is installed at the implantation site. Additional details regarding the replacement of a failed biological valve with a single-stent-valve are described in connection with FIGS. 5A-7B.

In some embodiments of the present invention, valve component 100 may be flexible and collapsible such that it can be collapsed, for example, during delivery via a catheter to the implantation site. Various embodiments of delivery systems and surgical approaches for minimally-invasive surgery are described below in connection with FIGS. 22A-26C. Upon delivery, the valve component may be at least partially expanded. FIG. 1A is a perspective view of valve component 100 in an expanded configuration. FIG. 1B is a perspective view of valve component 100 in a collapsed configuration. As used herein, "collapsed configuration" and "expanded configuration" refer to a relative difference in, for example, the diameter and/or any other physical characteristic(s) of a component (e.g., length, width). For example, the collapsed valve component shown in FIG. 1B has an reduced diameter and may or may not have a longer length than the expanded valve component shown in FIG. 1A.

Valve component 100 may include a biological material (e.g., tanned, untanned, heterologous or autologous), non-biological material, a synthetic material (e.g., polymer(s) such as polyurethane and/or silicon(es)), or a combination thereof. In some embodiments, valve component 100 may include preserved biological tissue such as, for example, human tissue (e.g., homografts, autografts of valve tissue) or animal tissue (heterograft or xenograft valve tissue). In some embodiments, valve component 100 may be a mechanical valve. For example, when valve component 100 is a biological valve, expansion of valve component 100 from a collapsed configuration to an expanded may require self-expansion of an affixed stent component 200. In contrast, a synthetic valve component 100 may be capable of self-expansion. Valve component 100 may have a shape/form (e.g., length, width, diameter, etc.) corresponding to that of the intended valve application (e.g., tricuspid, pulmonary, mitral or aortic). In FIGS. 1A and 1B, valve component 100 is a tricuspid valve with three flaps. This particular configuration may be particularly suitable, for example, for replacing a failed aortic valve. In other embodiments, valve component 100 may have any other suitable number of flaps and/or other physical characteristics (e.g., diameter, length, width, etc.).

FIG. 2A is a perspective view of stent component 200 in accordance with an embodiment of the present invention. As shown in FIG. 2B, stent component 200 houses valve component 100. In some embodiments, at least a portion of stent component 200 may be substantially cylindrical in shape. Alternatively or additionally, stent component 200 may have an indentation (e.g., annular groove) or other fixation element 202, for example, for fixing the stent in place at the implantation site. For example, when stent component 200 is part of double-stent-valve 400 (FIG. 4), fixation element 202 may matably attach to a complimentary fixation element 302 (e.g., inward annular projection, FIG. 3A) of stent component 300. When stent component 200 is part of a single-stent valve (FIG. 2B), fixation element 202 may affix to at least a portion of the failed valve. Additional embodiments of stent components that may include fixation elements are described in connection with FIGS. 6A and 8A-16.

In some embodiments of the present invention, stent component 200, like valve component 100, may be capable of at least two configurations: a first, collapsed configuration (e.g., during delivery) and a second, expanded configuration (e.g., after installation). FIG. 2A shows stent component 200 in an illustrative expanded configuration. FIG. 2C shows stent component 200 in an illustrative collapsed configuration, with the collapsed valve component 100 housed therein, for example, for delivery of both components to the implantation site at the same time. In some embodiments, stent component 200 may be made from wire or may be laser cut from a tube, sheath, or the like. Stent component 200 may include a shape-memory alloy material such as, for example, nitinol. The shape-memory alloy may allow for compression of stent component 200 (and/or valve component 100) into the first configuration for, for example, delivery through a small opening in the patient's body and expansion of stent component 200 to the second configuration during installation. Components 100 and/or 200 may be held in the collapsed configuration, for example, with a sheath or wrap. The sheath/wrapping may be removed in order to allow components 100 and/or 200 to reconfigure into the second configuration.

Valve component 100 may be secured to stent component 200 via any suitable securing mechanism or combination of securing mechanisms. For example, in one embodiment, valve component 100 may be sutured with one or more stitches to stent component 200. In another embodiment, valve component 100 may be secured to stent component 200 by way of a friction fitting. For example, valve component 100 may have a fully-expanded diameter that is slightly larger than the expanded diameter of stent component 200 such that components 100 and 200 fit securely together upon expansion of component 100 within component 200. In yet another embodiment, a hook-and-loop type (e.g., VELCRO®) fastening system may be used to secure valve component 100 to stent component 200. For example, stent component 200 may include microscopic hooks and valve component 100 may include corresponding microscopic loops (or vice-versa). This hook-and-loop fastening system may include a micro-velour material, which has been used previously for surgical applications to improve tissue in-growth. Such a hook-and-loop fastening system may allow the position of valve component 100 to be fine-tuned relative to the position of stent component 200, for example, after components 100 and 200 have been implanted within a patient's body. The hooks/loops may also facilitate blood clotting and the formation of a seal at the interface between valve component 100 and stent component 200. To avoid premature clot formation (e.g., excessive clot formation before installation is complete), anti-coagulation monitoring and/or treatment may be provided to the patient. Reliable hook-and-loop connections may still be achieved in the presence of premature clot formation, although higher activation pressure (described below) may be required. A preliminary evaluation shows that reliable hook-and-loop connections can be formed in the presence of water, jelly, liquid soap, and/or coagulating proteins. In some embodiments, such a hook-and-loop fastening system may be used, alternatively or additionally, to secure stent component 200 to stent component 300 (e.g., with the microscopic hooks attached to an exterior surface of stent component 200 and the corresponding microscopic loops attached to an interior surface of stent component 300, or vice versa).

Any suitable mechanism or combination of mechanisms (e.g., direct or indirect exertion of mechanical compression) can be used to supply the activation pressure required to cause the micro-hooks to attach to the micro-loops. For example, in some embodiments, one or more balloons may be positioned adjacent to valve component 100 and/or stent component 200 (e.g., within valve component 100) and inflated temporarily to bring the micro-hooks into contact with the micro-loops. Such balloon(s) may placed within the valve component 100 and/or stent component 200 subsequent to delivery of the stent and/or valve to the implantation site. Alternatively, in some embodiments the balloon(s) can be mounted (e.g., removably mounted) within the valve component 100 and/or stent component 200 prior to delivery of the stent and/or valve to an implantation site (e.g., prior to loading the stent and/or valve into a delivery device). The use of such balloon(s) is not limited to embodiments in which the valve and stent are affixed to one another by way of hooks/loops. Rather, such balloon(s) may be used whenever it is necessary or desirable to use the balloon(s) to aid in the expansion and/or engagement at the implantation site of the stent and/or valve (e.g., when the valve is sutured to the stent). In some embodiments, a self-expanding valve component 100 may be provided that self-expands within stent component 200 in order to cause the micro-hooks to contact the micro-loops.

FIG. 3A is a perspective view of stent component 300 in accordance with an embodiment of the present invention. As described above, stent component 300 may have a fixation element 302 (e.g., inward annular projection) that matably attaches to a complimentary fixation element 202 of stent component 200 (FIG. 2A). FIG. 4 shows an embodiment of such matable attachment, in which component 300 houses both components 100 and 200 to form double-stent-valve 400. The geometry (e.g., length, width(s), diameter(s), etc.) of stent component 300 may be particularly suited, for example, for aortic valve replacement. In other embodiments, other geometries and configurations of stent component 300 may be provided.

Stent component 300 may be secured in place at the implantation site using any suitable securing mechanism or combination of securing mechanisms. For example, in some embodiments, fixation element 302 may form a recess (e.g., exterior annular groove) for receiving at least a portion of the failed valve. In some embodiments, stent component 300 may have a diameter slightly larger than a diameter of the implantation site such that delivery and expansion of stent component 300 at the implantation site secures stent component 300 in place by way of a friction fitting. In some embodiments, stent component 300 may include one or more projections (e.g., spikes) or clasps for anchoring stent component 300 to the failed valve and/or adjacent structure(s) at the implantation site.

Figure 5A:
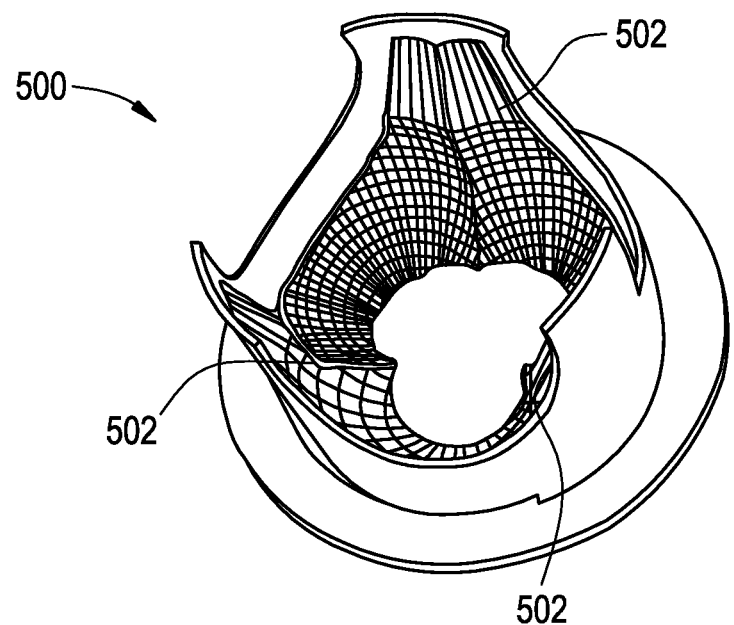
FIGS. 5A-7B illustrate the use of a single-stent-valve to replace a failed biological (artificial) valve according to some embodiments of the present invention.
Figure 5B:
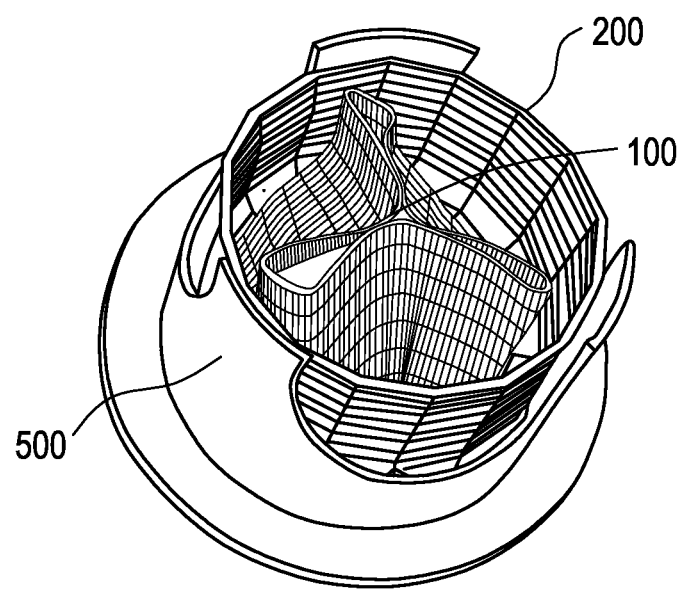

FIGS. 5A-7B illustrate embodiments of the present invention for replacing a failed artificial (e.g., biological) valve (e.g., stent-valve) introduced to a patient's body during a prior surgery. FIG. 5A is a perspective view of a failed biological valve 500 where leaflets 502 of the valve fail to close. FIG. 5B is a perspective view of the failed biological valve 500 after implantation of the stent-valve shown in FIG. 2B. As shown, failed biological valve 500 (e.g., and/or its accompanying stent) secure the new stent-valve in place at the implantation site. More particularly, fixation element 202 of the stent-valve (FIGS. 2A and 2B), which may be an annular groove forming the narrowest portion of the stent-valve, may receive the annulus of failed biological valve 500 thereby securing the stent-valve in place. In other embodiments of the present invention, at least a portion of failed biological valve 500 may be removed from the patient's body (e.g., the failed valve itself), whereas other portion(s) of the failed valve may be left behind at the implantation site (e.g., a supporting stent). In still other embodiments, the failed biological valve 500 including all of its associated component(s) may be substantially entirely removed from the implantation site prior to installation of the new stent-valve.

Figure 6A:
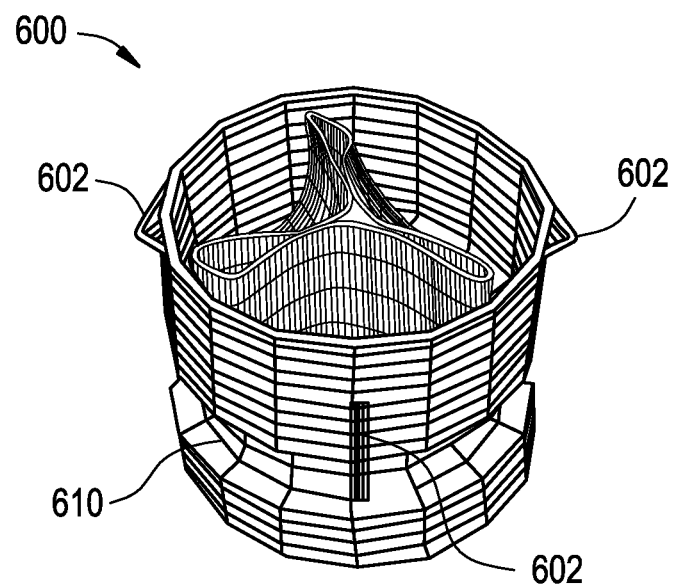
Figure 6B:
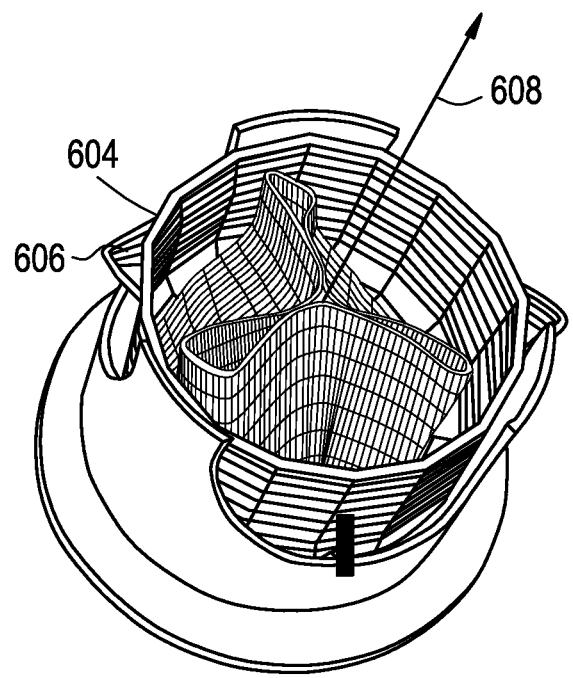

FIG. 6A is a perspective view of another example of a stent-valve 600 in accordance with an embodiment of the present invention. FIG. 6B is a perspective view showing a use of stent-valve 600 to replace a failed artificial (e.g., biological) valve. Stent-valve 600 includes one or more (e.g., three) locking or retaining elements 602 along an outer surface of the stent component. Each locking element 602 may include directionality such that it collapses (e.g., becomes flush with an outer surface of the stent component) upon engagement of the locking element with another surface (e.g., the interior of a catheter). When a locking element 602 protrudes from the outer surface of the stent component, a first end 604 of the locking element may be adjacent to the outer surface of the stent component, while a second end 606 of the locking component may be spaced apart from the outer surface of the stent component. When multiple locking elements 602 are provided, first ends 604 of all the locking elements may be positioned at substantially the same vertical height/position along the central axis of the stent component (e.g., albeit dispersed evenly around the perimeter of the stent component), and second ends 606 may be positioned at different vertical height(s)/position(s) than first ends 604. First end 604 may be flexible (e.g., allowing hinge-like movement in two dimensions) such that movement of the second end relative to the outer surface of the stent component does not impair the locking mechanism.

In some embodiments of the present invention, stent-valve 600 may be inserted into the interior of the failed valve in the direction of arrow 608 in FIG. 6B. When first end 604 of each locking element 602 encounters the interior diameter/annulus of the failed valve, second end 606 of the locking element may collapse toward the outer surface of the stent component. Upon second end 606 of the locking element reaching an open area of the failed valve, the second end may jut outwardly, locking stent-valve 600 in place. Thus, locking elements 602 may provide a mechanism for securing the new stent-valve in place, as an alternative to or in addition to fixation element 610 (e.g., annular groove) of the stent component for affixing stent-valve 600 to (for example) the annulus the failed valve.

Figure 7A:
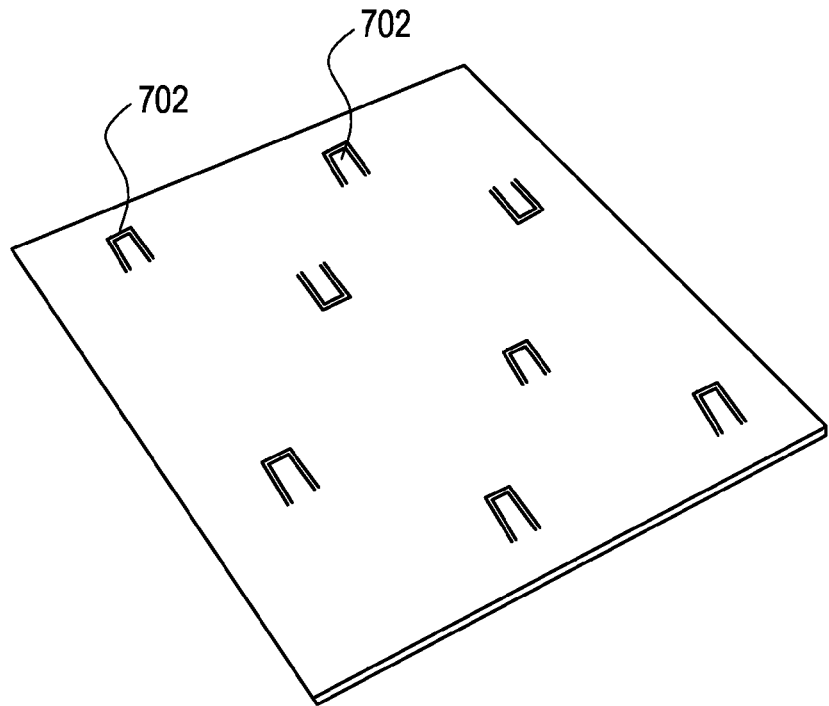
Figure 7B:
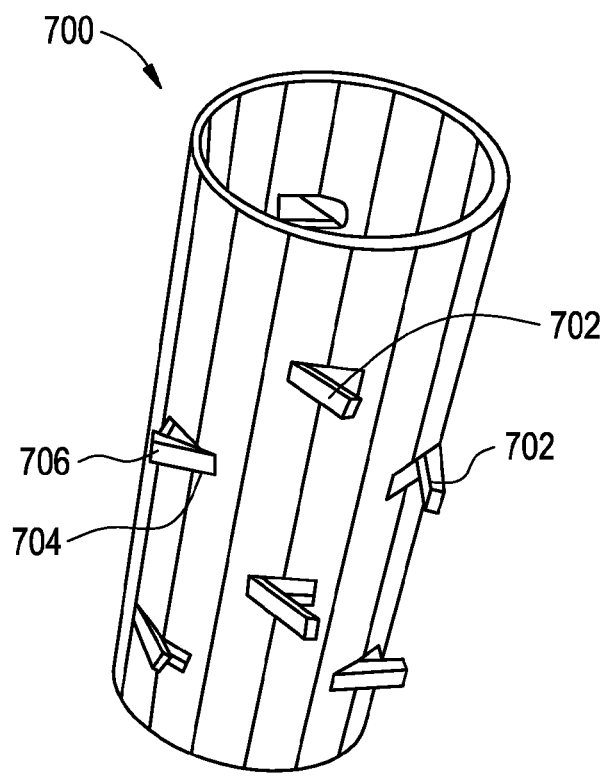

FIGS. 7A and 7B show another embodiment of a stent component 700 with locking elements in accordance with the present invention. FIG. 7A shows that such a stent component can be made from, for example, a sheet of suitable material (e.g., nitinol). Referring to FIG. 7B, stent component 700 includes one or more locking elements 702 that extend radially from an outer surface of the stent component such that, for each locking element, first end 704 and second end 706 of that locking element have substantially the same vertical position/height along the central axis of the stent component. In other embodiments, such locking elements may be slightly angled, such that ends 704 and 706 of the same locking element have different relative vertical positions/heights along the central axis of the stent component. In some embodiments, a stent component may be provided that includes multiple locking elements, with each locking element having ends 704 and 706 with different angular orientations. Different locking elements 702 may have the same or different vertical positions/heights along the central axis of the stent component.

FIGS. 8A-16 show additional examples of suitable stent components for use in valve replacement in accordance with some embodiments of the present invention. These stent components may be used, for example, as part of single-stent-valves and double-stent-valves. Each of these stent components includes one or more attachment elements for removably attaching the stent component (e.g., together with an integrated valve component) to a delivery device (FIGS. 22-26). In some embodiments, these stent components may also include a fixation element (e.g., similar to fixation element 202 (FIG. 2A)) for fixing the stent component in place at the implantation site.

Figure 8A:
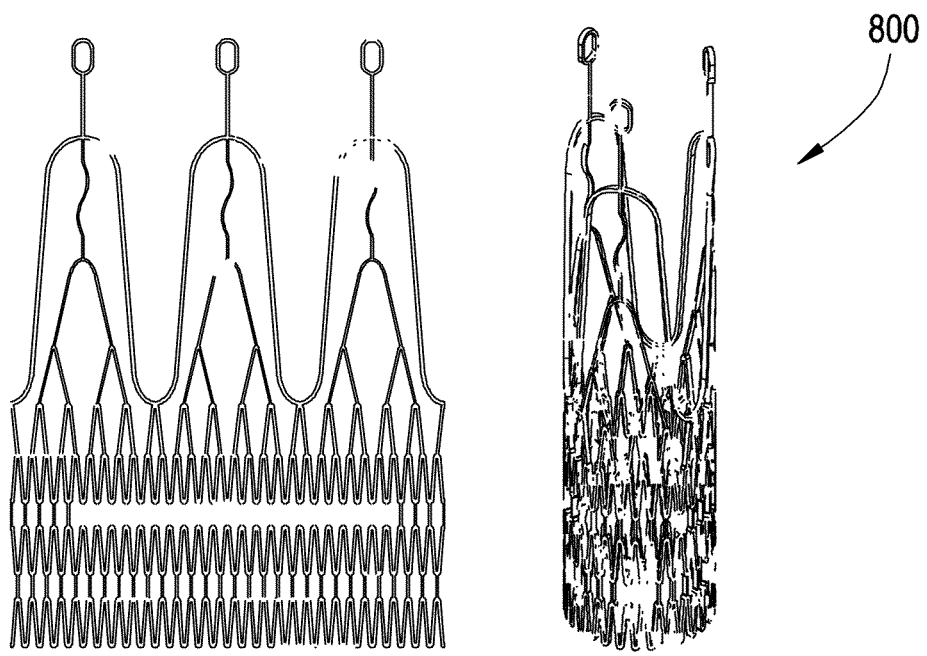
FIGS. 8A and 8B show a stent component that includes attachment elements for securing the stent to a delivery device and fixation elements for securing the stent at the implantation site according to some embodiments of the present invention.
Figure 8B:
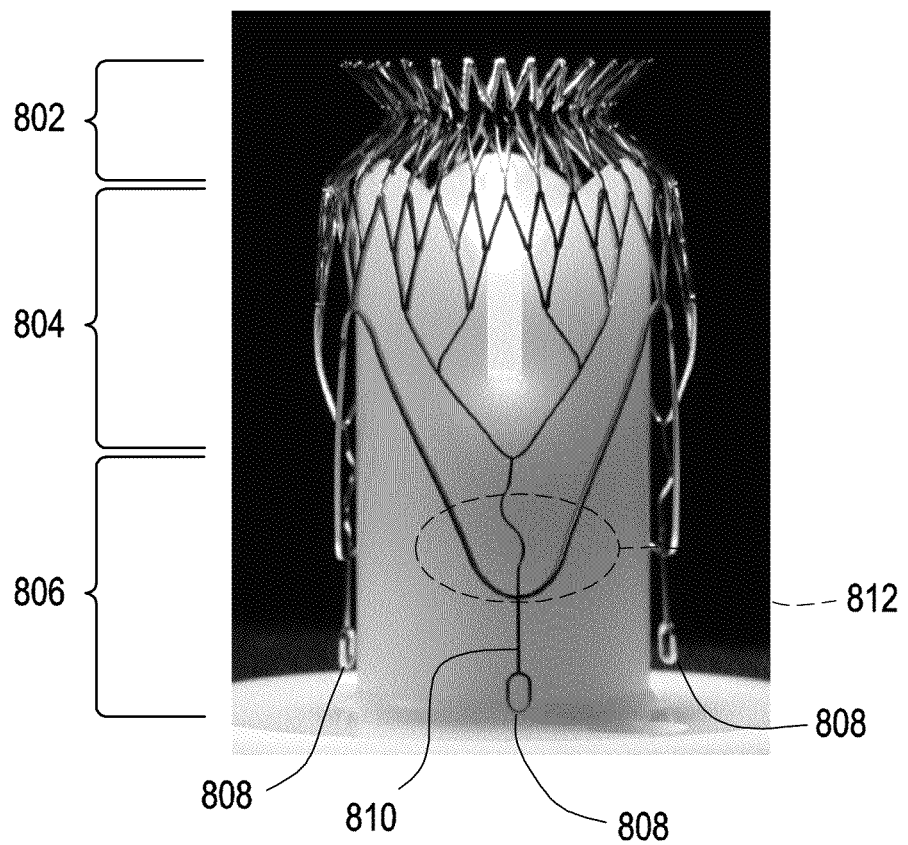

FIG. 8A shows a perspective view of a stent component 800 in a collapsed configuration, as well as an as-cut view of stent component 800 that illustrates details regarding its structure. FIG. 8B shows stent component 800 in an expanded configuration. Stent component 800 includes first (e.g., proximal) section 802 that includes a fixation element (e.g., annular groove), second section 804 that may follow the contour of a valve component to be housed therein, and third (e.g., distal) section 806 that includes one or more (e.g., three) attachment elements 808. In some embodiments, stent component 800 may include (for example) a lattice structure (e.g., formed from nitinol wire), for example, with section 802 having a denser population of lattice cells than section 804 and/or section 806. This may provide added support to the fixation element in section 802 and therefore increase the stability of device 800 at the implantation site. In some embodiments, stent component 800 may include only closed lattice cells in order to facilitate the recapture of stent component 800 by a delivery device when stent component 800 is in a partially-expanded configuration (described below).

In some embodiments, each of attachment elements 808 may include an opening (e.g., circular or ovular) for removably attaching stent component 800 to a complimentary element (e.g., wire, strap or hook) of a delivery device. Attachment elements 808 may allow for partial expansion of the stent component (e.g., together with an integrated valve component and/or another stent component) within a patient's body while causing the stent component to remain attached to the delivery system. For example, sections 802 and 804 (e.g., and part of section 806) of stent component 800 may expand when stent component 800 is partially released from a shaft during delivery, whereas no change may be observed to the relative positions of attachment elements 808 still constrained by the shaft (e.g., see FIG. 28 "partial release"). This may allow a surgeon to reposition and/or test the functionality of the stent-valve (or double-stent-valve) within the patient's body before finalizing deployment of the stent-valve at the implantation site. Such testing of the valve functionality may include peripheral pulse monitoring, whereby a pulse wave is measurable if the valve is functioning properly. A more reliable assessment of the stent valve function can be made with transesophageal echocardiography (TEE), intravascular ultrasound (IVUS) and/or intracardiac echocardiography (ICE). If the stent-valve malfunctions during the test (e.g., if the valve does not permit sufficient blood-flow), the stent-valve may be fully recaptured by the delivery device and retrieved from the patient's body. In other embodiments, stent component 800 may have a different lattice structure, attachment elements 808 may be reduced or enlarged in length and/or other dimension(s), and/or attachment elements 808 may be included in other location(s) relative to stent component 800 (e.g., within section 804).

Figure 8C:
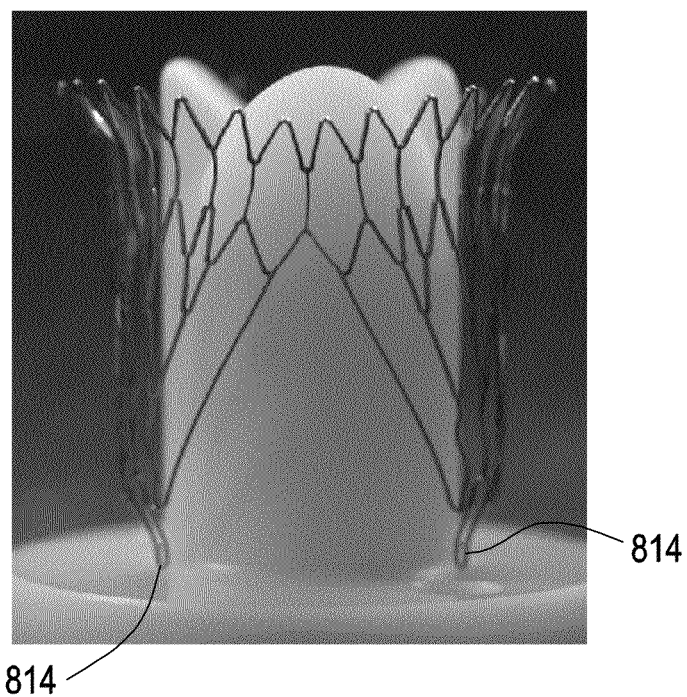
FIG. 8C shows a stent component having a diameter in the region of the attachment element(s) that is smaller than the diameter of a stent region that houses an associated valve, according to some embodiments of the present invention.

FIG. 8C shows another embodiment of a stent component with integrated attachment elements 814 that are configured such that the fully expanded diameter in the region of the attachment element(s) is smaller than the diameter of the region that houses an associated valve. As shown in this example, the attachment elements project partially inwardly toward the center axis of the stent component. This may reduce the risk of injury to the patient's body (e.g., perforation of the aorta) from the attachment elements. Alternatively or additionally, this may make it easier to affix the attachment elements to a complimentary structure of the delivery device. For example, when the device is collapsed for attachment to the delivery device, the reduced diameter within the region of the attachment elements may cause the attachment elements to engage the stent holder earlier.

Figure 8D:
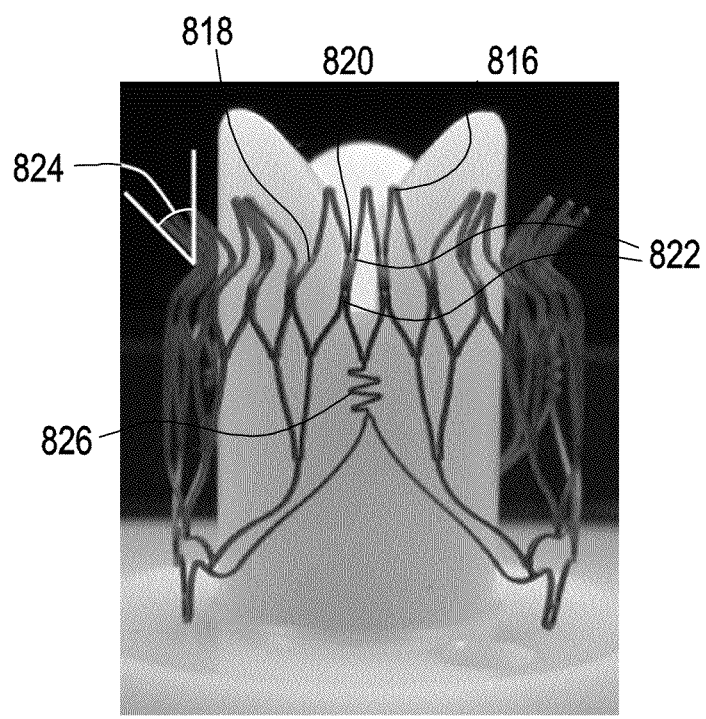
FIG. 8D shows a stent component that includes independently bendable element(s) for use in positioning/securing the stent to the geometry/topology at an implantation site according to some embodiments of the present invention.

FIG. 8D shows yet another embodiment of a stent component in accordance with the present invention. In this embodiment, the first (proximal) section of the stent includes 27 independent, bendable elements 816, each of which may include connected and/or disconnected cell(s) which can be open and/or closed. In this embodiment, each bendable element includes a single, closed cell. In other embodiments, other number(s) and/or configuration(s) of the bendable elements may be provided. Bendable elements 816 allow for accurate positioning/securing of the proximal stent section to the geometry/topology of (for example) a calcified annulus/failed biological valve. Each element 816 can bend/adapt independently to the topology of the immediately adjacent portion of the calcified annulus/failed biological valve. Bendable elements 816 collectively form an annular groove in which the location of the bending deformation (grooved portion) for each bendable element is controlled by reducing or elongating the lengths of an attached pair of stent struts (818, 820) which act as a joint. The length of a single stent strut is shown by numeral 822. Primarily, the radial force/resistance of each bendable element 816 is influenced by the selection of angle 824 during stent manufacturing. Other design parameters such as strut thickness/width also influence the radial force. An advantage of this design is that the stent proximal section can more adequately anchor the stent in place at the implantation site independently of the stent mid section. Thus, the stent mid section can be designed to accommodate (for example) the aortic valve without any over sizing, therefore reducing the risk of valve failure due to long term mechanical stress. The stent of FIG. 8D also includes compensation element 826 (e.g., including a triangular wave portion and two elongate arms) for accommodating elongation mismatch (if any) within the stent during manufacturing and/or crimping. Contrast FIG. 8D with the embodiment shown in FIG. 8C, in which the absence of dedicated pairs of struts prevents the stent proximal section from having elements that bend independently (e.g., during implantation).

Figure 8E:
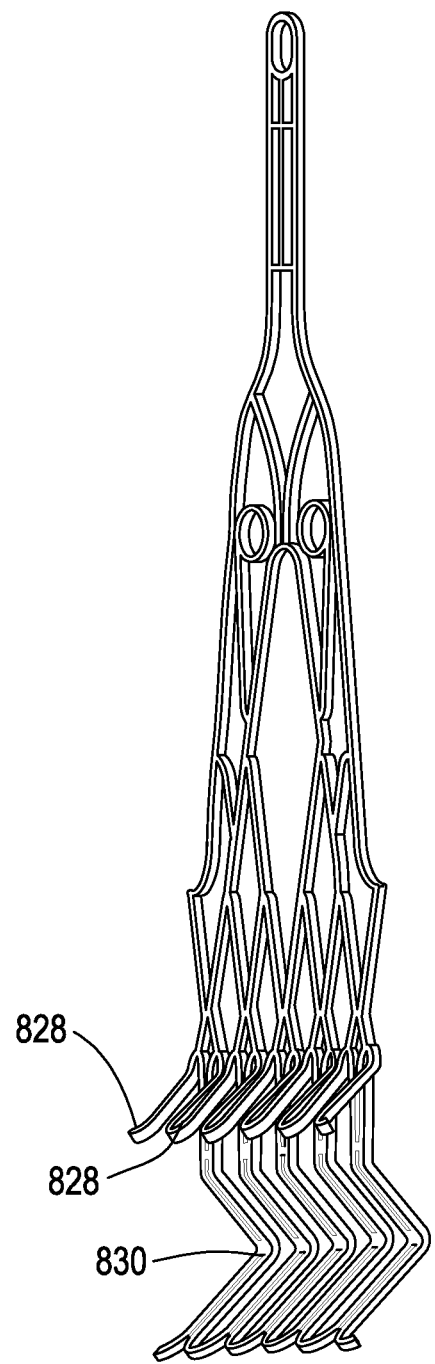
FIG. 8E shows a stent component that includes locking elements in a crown configuration and a fixation element for securing the stent at an implantation site according to some embodiments of the present invention.

FIG. 8E shows another embodiment of a stent component in accordance with the present invention. In FIG. 8E, only about ⅓ of an as-cut view of the stent component is shown in order to more clearly show its features. Similar to the locking/retaining elements 602 shown in FIGS. 6A and 6B, the stent component shown in FIG. 8E includes a plurality of independently bendable locking elements 828 generally located within the region of the stent component referenced as region 804 in FIG. 8B. Locking elements 828 form a crown that may engage, for example, a failed biological valve or calcified native annulus from the outflow side. The stent component in FIG. 8E also includes fixation element 830 (e.g., annular groove). In FIG. 8E, locking elements 828 are shown as being positioned at substantially the same position/height along the central axis of the stent component. In other embodiments, different locking elements 828 may have the same or different vertical positions/heights along the central axis of the stent component similar to, for example, the stent shown in FIG. 7B. Having different positions/heights for at least some of locking elements 828 may facilitate engagement with, for example, native valves of different sizes (e.g., a thin native valve which can be engaged by locking elements separated by a small distance or a thick native valve which can only be engaged by more distantly spaced locking elements).

Figure 8F:
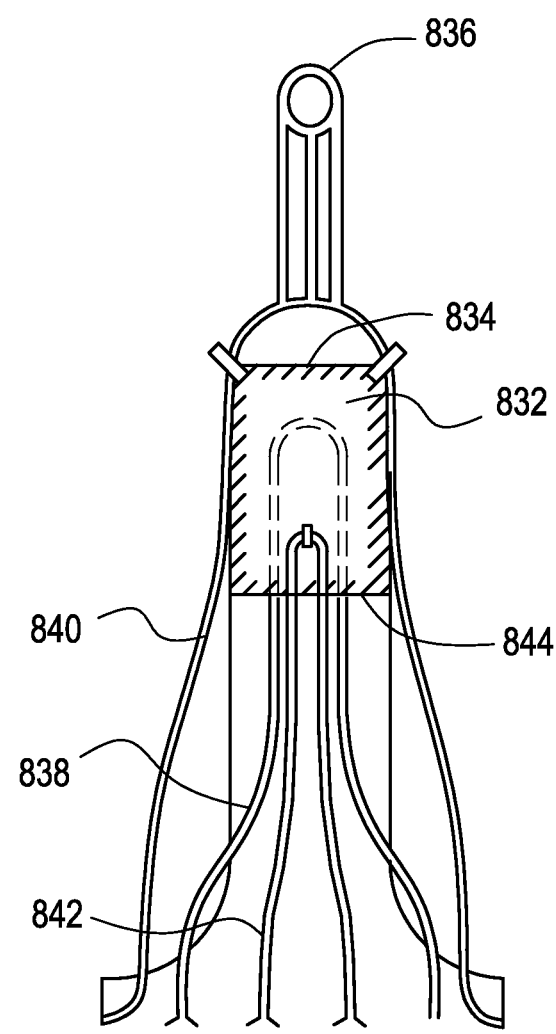
FIG. 8F shows a stent component that includes multiple struts for carrying a valve component more closely to a region of the stent component that includes attachment element(s) for attaching the stent component to a delivery device.

FIG. 8F shows another embodiment of a stent component in accordance with the present invention. In FIG. 8F, only about ⅓ of an as-cut view of the stent component is shown in order to more clearly show its features. FIG. 8F includes a Dacron pocket 832 for housing a valve component, where Dacron pocket 832 is sutured along the valve free edge 834. As shown, the valve component within pocket 832 is housed more closely to attachment element(s) 836, which are similar to attachment elements 808 in FIG. 8B, in the embodiment of FIG. 8F than in the embodiment shown in FIG. 9C. A middle inverted U-shaped strut 838 is slid into Dacron pocket 832. The valve/pocket is sutured to an outer inverted U-shaped strut 840. Inner U-shaped strut 842 is positioned outside Dacron pocket 832 and serves as a skid during loading/releasing/recapturing of the implant with a delivery device by reducing the friction forces between Dacron pocket 832 and the outer sheath. Inner U-shaped strut 842 may also be sutured to Dacron pocket 832. In some embodiments, Dacron pocket 832 may be closed with further stitching 844. Although the bottom portion of the stent is not shown in FIG. 8F, in some embodiments it may include, for example, a fixation element (e.g., annular groove) similar to fixation element 802 in FIG. 8B.

Figure 9A:
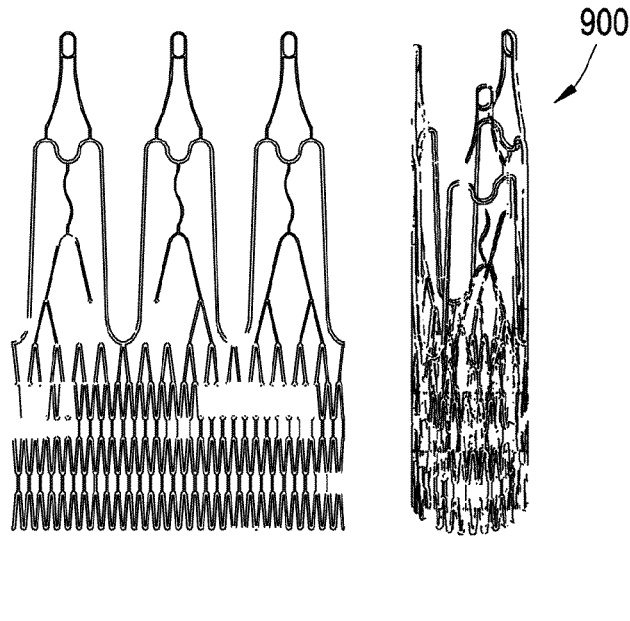
FIGS. 9A-16 show additional embodiments of stent components that include attachment elements for securing the stent to a delivery device and/or fixation elements for securing the stent at the implantation site according to the present invention.
Figure 9B:
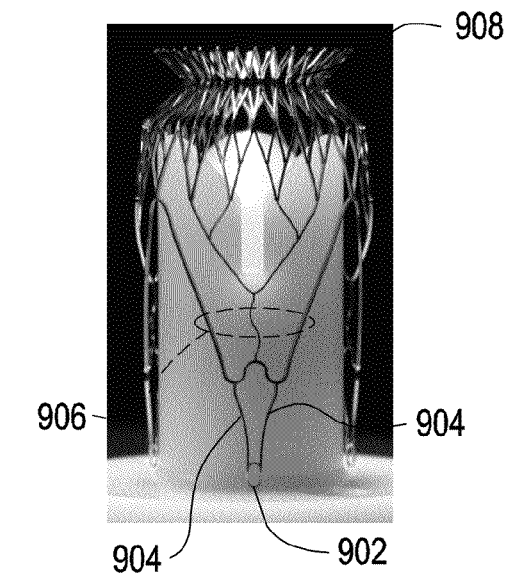
Figure 9C:
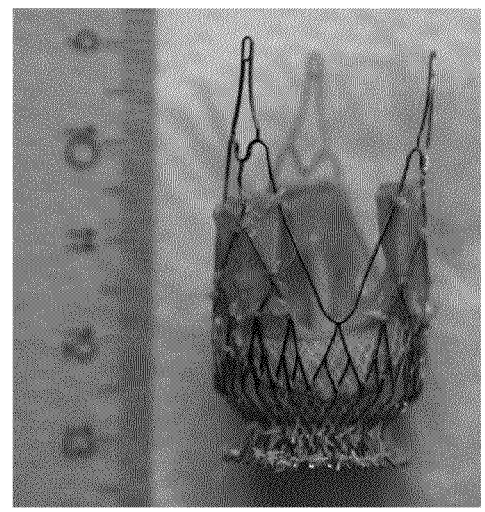

FIGS. 9A-9C show another example of a stent component 900 with integrated attachment element(s) 902 in accordance with an embodiment of the present invention. FIG. 9A shows a perspective view of stent component 900 in a collapsed configuration, as well as an as-cut view of stent component 900 that illustrates details regarding its structure. FIG. 9B is a perspective view of stent component 900 in an expanded configuration. FIG. 9C shows stent component 900 (with an integrated valve component) positioned beside a ruler to show its size (e.g., about 4 centimeters). As shown, each of attachment elements 902 includes a circular or ovular opening attached to stent component 900 by two supporting elements 904 (e.g., wires). In turn, each pair of supporting elements 904 attaches to a stem 906 (e.g., commissural post) within the lattice structure. In contrast, each of the attachment elements 808 in FIG. 8B attaches to stent component 800 by a single supporting element 810, and each supporting element 810 is attached to a stem 812. All of the stent components shown in FIGS. 8A-16 include three stems, although it will be understood that other suitable numbers of stems or no stems at all (e.g., FIG. 2A) may be provided in accordance with some embodiments of the present invention. Stent component 900 also includes a fixation element 908, which may be substantially similar to fixation element 202 (FIG. 2A). In the embodiment of FIG. 9C, the valve component is sutured around the circumference of its annulus. Each of the three leaflets of the valve component is also spot-sutured to the stent to permit valve functionality. The locations of the sutures may be selected in order to permit elongation of the stent during crimping without damaging the valve or suture. For example, the inflow of stent (e.g., within region 802 shown in FIG. 8B) may be covered on its inner side with a cloth (e.g., mesh). The cloth and valve component may be sutured to the stent (e.g., using a running and/or interrupted technique) in the region adjacent to the annular groove (e.g., along the border of stent sections 802 and 804 in FIG. 8B). Some excess cloth on the inflow side may be folded over onto the exterior side of the stent and sutured together with the valve component in the vicinity of (e.g., further towards section 804) the previous suturing location. The commissures of the valve component may also be attached to the corresponding stent posts, which may have previously been covered with cloth (e.g., Dacron). Alternatively, pericardium or other suitable material can be used to cover the stent component. In some embodiments, the valve component may be a porcine valve component which may be harvested as such or assembled from various donors in order to have an optimal match between three cusps. Bovine and equine valves may also be used that are made from pericardium. Other suitable sources of valve components can also be used.

Figure 10A:
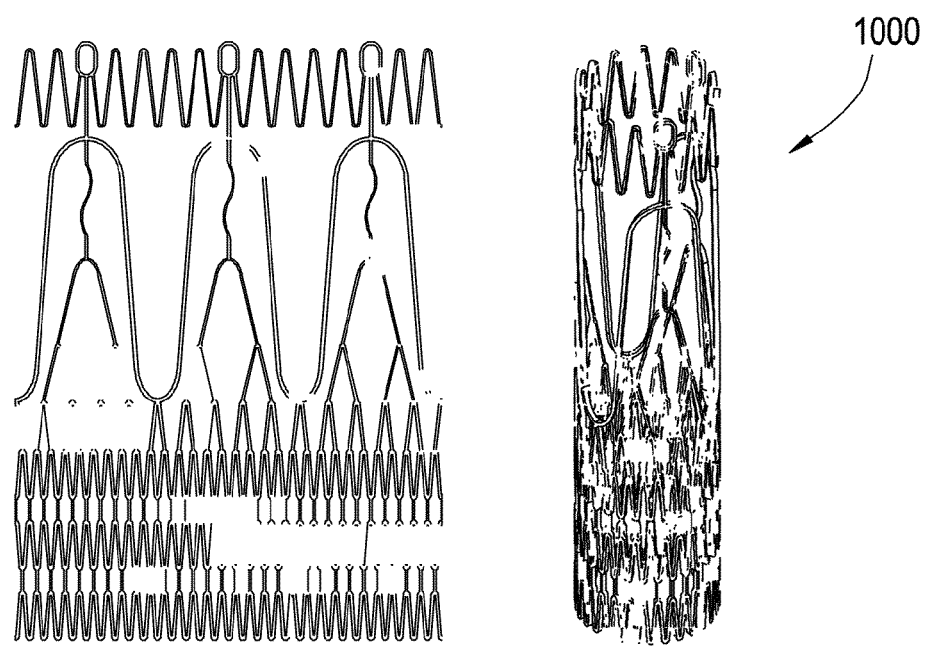
Figure 10B:
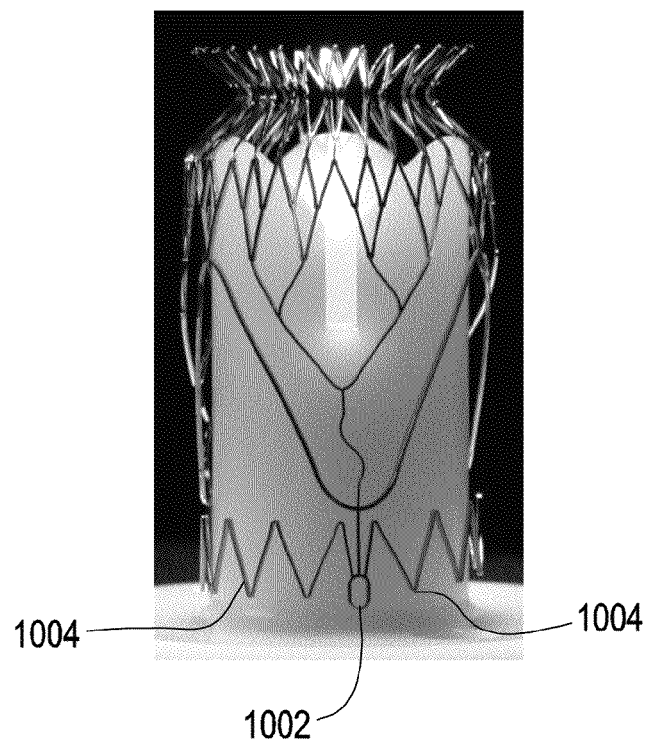

FIGS. 10A-10B show yet another example of a stent component 1000 with integrated attachment element(s) 1002 in accordance with an embodiment of the present invention. FIG. 10A shows a perspective view of stent component 1000 in a collapsed configuration, as well as an as-cut view of stent component 1000 that illustrates details regarding its structure. FIG. 10B is a perspective view of stent component 1000 in an expanded configuration. As shown, at least one pair (e.g., all pairs) of attachment elements 1002 are attached to one another with a bracing element 1004. Each bracing element 1004 may attach on one end to a first attachment element 1002 and on the other end to a second attachment element 1002. In some embodiments, the bracing element(s) 1004 may include a wire shaped like a triangular wave. When all attachment elements 1002 include a bracing element 1004, collectively the bracing elements 1004 may form a circle around the perimeter of stent component 1000. Stent component 1000 may be substantially the same as stent component 800 (FIG. 8B) in all other respects.

FIGS. 11-16 show additional examples of stent components with integrated attachment element(s) in accordance with some embodiments of the present invention. Each of FIGS. 11-16 includes a perspective view of a stent component in a collapsed configuration, as well as an as-cut view of the stent component that illustrates details regarding its structure. The following description summarizes various features of the stent components shown in FIGS. 11-16. Additional structural features of the embodiments shown in FIGS. 8A-16 will be apparent to one of ordinary skill in the art from the drawings.

Figure 11:
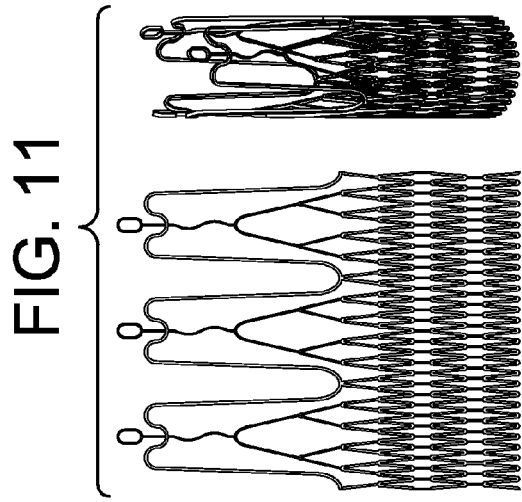

FIG. 11 shows a stent component that includes shorter supporting element(s) for attaching to a corresponding number of ovular/circular attachment element(s) (i.e., shorter in comparison to supporting elements 810 of FIG. 8B). The stem(s) in FIG. 11 for attaching to the supporting elements may be substantially the same as stems 906 in FIG. 9B.

Figure 12:
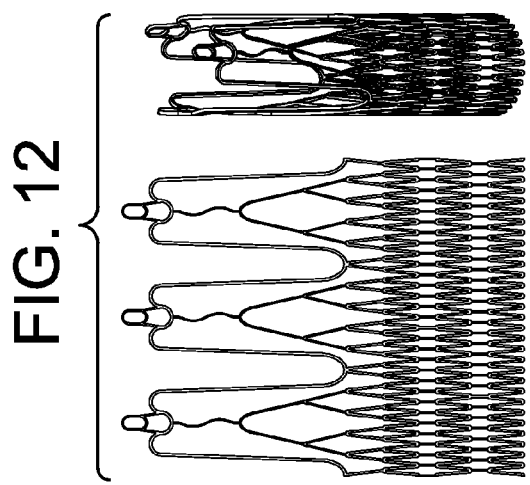

FIG. 12 shows a stent component that includes two supporting elements for attaching to each ovular/circular attachment element. Each pair of supporting elements attaches to a stem such that collectively the supporting elements and stem form a second ovular/circular opening, for example, for added support and/or for use as an additional or alternative attachment element. The stem(s) in FIG. 12 may be substantially the same as stems 906 in FIG. 9B.

Figure 13:
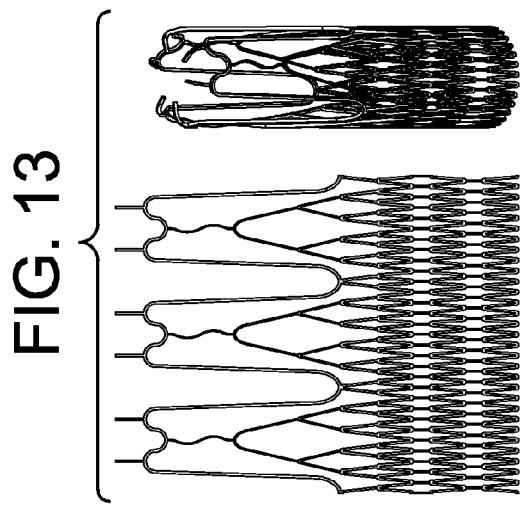

FIG. 13 shows a stent component that includes non-circular/ovular attachment components such as, for example, wires, hooks, straps, or a combination thereof for matably attaching to a complimentary element of a delivery device (e.g., a circular or ovular opening). The stent component in FIG. 13 also includes an increased number of attachment elements (e.g., six) when compared to the number of attachment elements (e.g., three) of stent component 900 (FIGS. 9A and 9B). In FIG. 13, the attachment elements attach directly to the stems of the stent component, two attachment elements per stem. The stem(s) in FIG. 13 may be substantially the same as stems 906 in FIG. 9B.

Figure 14:
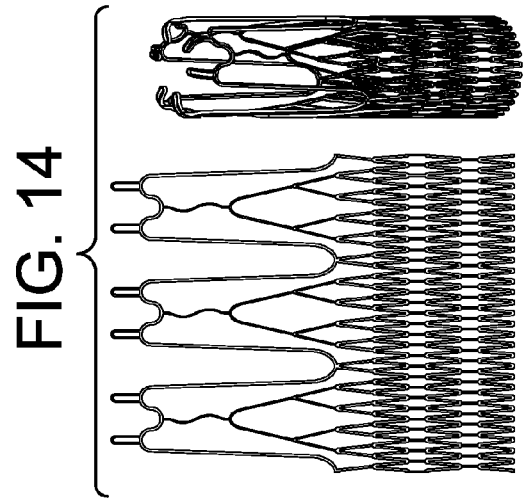

FIG. 14 shows a stent component that replaces the wire/hook attachment elements in FIG. 13 with long, narrow openings (e.g., long and narrow in comparison to attachment elements 902 of FIG. 9A). The stem(s) in FIG. 14 may be substantially the same as stems 906 in FIG. 9B.

Figure 15:
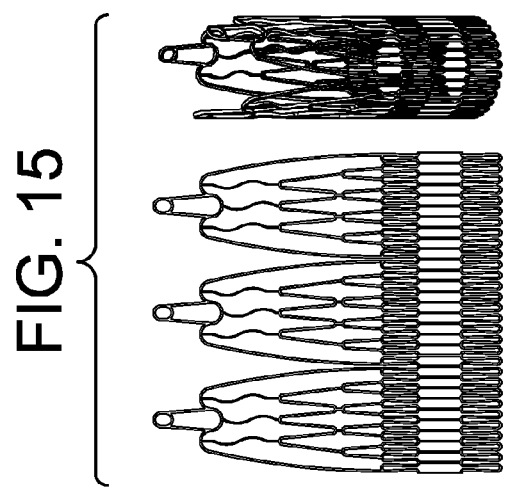

FIG. 15 shows a stent component with a modified lattice structure, including a modified stem structure. The stent component in FIG. 15 also includes circular/ovular attachment elements, where each attachment element is attached to a stem by two supporting elements. Each pair of supporting elements and corresponding stem may form a second circular/ovular opening, in a manner similar to the supporting element/stem configuration shown in FIG. 12.

Figure 16:
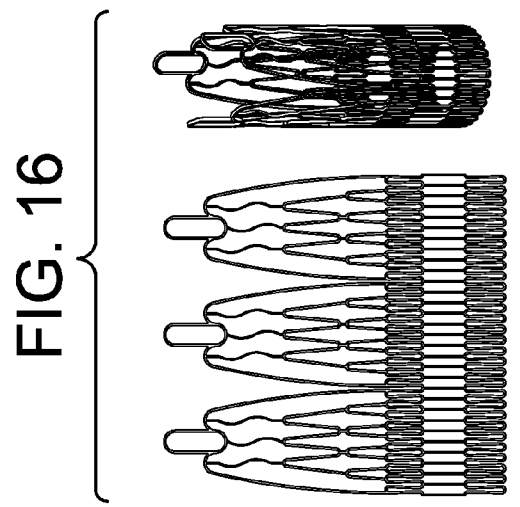

FIG. 16 shows a stent component with attachment elements modified relative to the attachment elements shown in FIG. 15. Each attachment element in FIG. 16 includes a wire (e.g., a "U"-shaped wire), with both ends of the wire attaching directly to the same stem such that the attachment element/stem configuration forms a substantially ovular/circular opening. The stem(s) in FIG. 16 may be substantially the same as the stems shown in FIG. 15.

Figure 17:
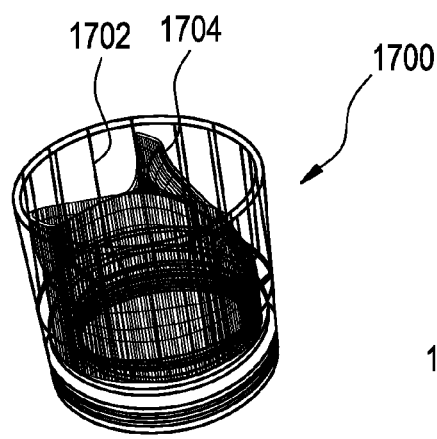
FIGS. 17/18, 19, and 20 show additional examples of double-stent-valves according to some embodiments of the present invention.
Figure 18:
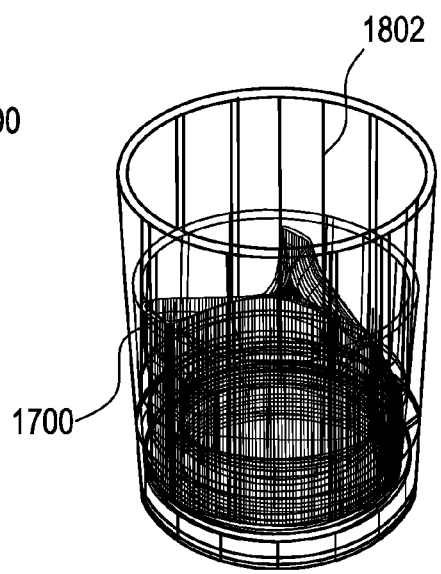

FIGS. 17/18, 19 and 20 show additional examples of double-stent-valves in accordance with some embodiments of the present invention. Single-stent valve 1700 of FIG. 17 includes stent 1702 and valve component 1704. FIG. 18 shows a double-stent valve that includes stent-valve 1700 and positioning stent 1802, which may be attached together by way of (for example) an annular groove and corresponding annular recess. Stent component 1802 may be covered with, for example, pericardium in order to prevent paravalvular leaking. The double-stent-valve of FIG. 18 may have a generally cylindrical shape that is suitable for, for example, pulmonary and/or aortic applications.

Figure 19:
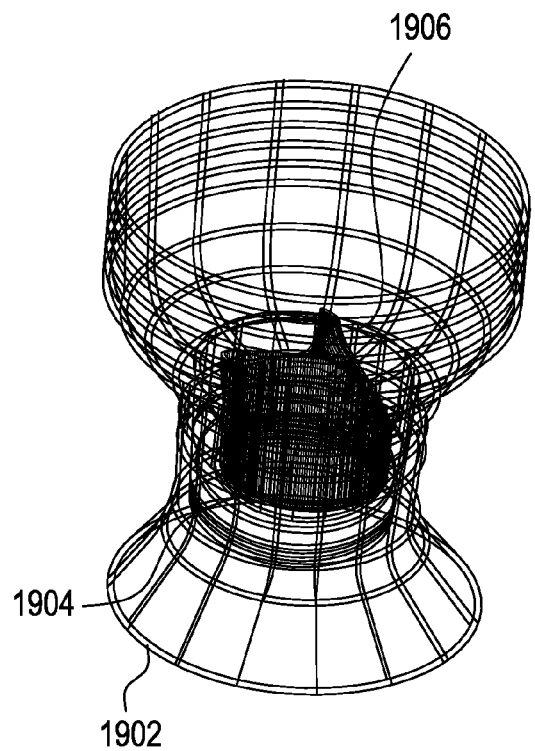
Figure 20:
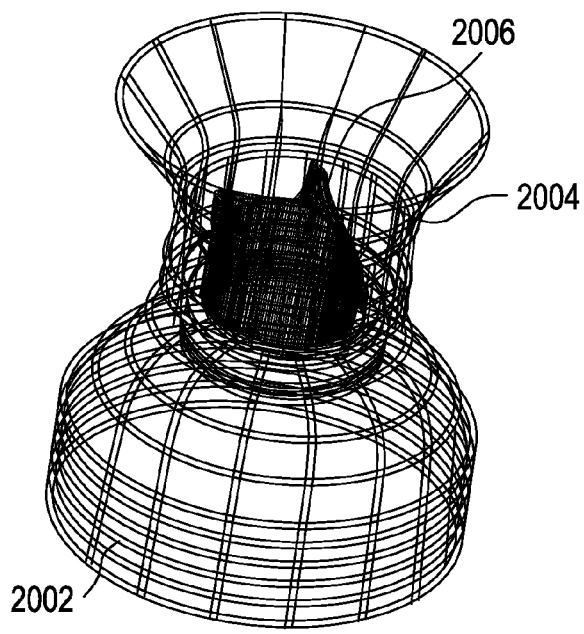

Now referring to FIGS. 19 and 20, FIG. 19 shows a double-stent-valve with first stent 1902, second stent 1904, and valve component 1906. FIG. 20 shows a double-stent-valve with first stent 2002, second stent 2004, and valve component 2006. Again, the positioning stents in FIGS. 19 and 20 may be covered (e.g., with pericardium) in order to prevent paravalvular leaking. The stents of FIGS. 19 and 20 may be suitable for, for example, pulmonary valve replacement (e.g., in the presence of an aneurysm that creates a deformation and where there is no suitable rim for placement of a grooved stent-valve). More particularly, with respect to pulmonary valve applications, many candidates for pulmonary valve replacement have an aneurysm there or a funnel-type configuration at the inflow or at the outflow. Thus, the first stent 1902 or 2002 can adapt to this funnel-type pulmonary artery configuration and provide the round orifice for securing the stent-valve (1904, 1906) or (2004, 2006). In some embodiments, a double-stent-valve similar to the double-stent-valve of FIG. 20 may be provided that is suitable for mitral and/or tricuspid valve applications, where the positioning stent has a reduced height and an oval configuration that provides a round rim for attachment to a groove of a stent-valve (alternatively, a hook-loop fastening system can be used). Alternatively or additionally, the positioning stent may have independently bendable elements that provide a secure fit at the implantation site. Additional structural features of the embodiments shown in FIGS. 17-20 and details regarding their use for valve replacement will be apparent to one of ordinary skill in the art from the drawings.

Figure 21A:
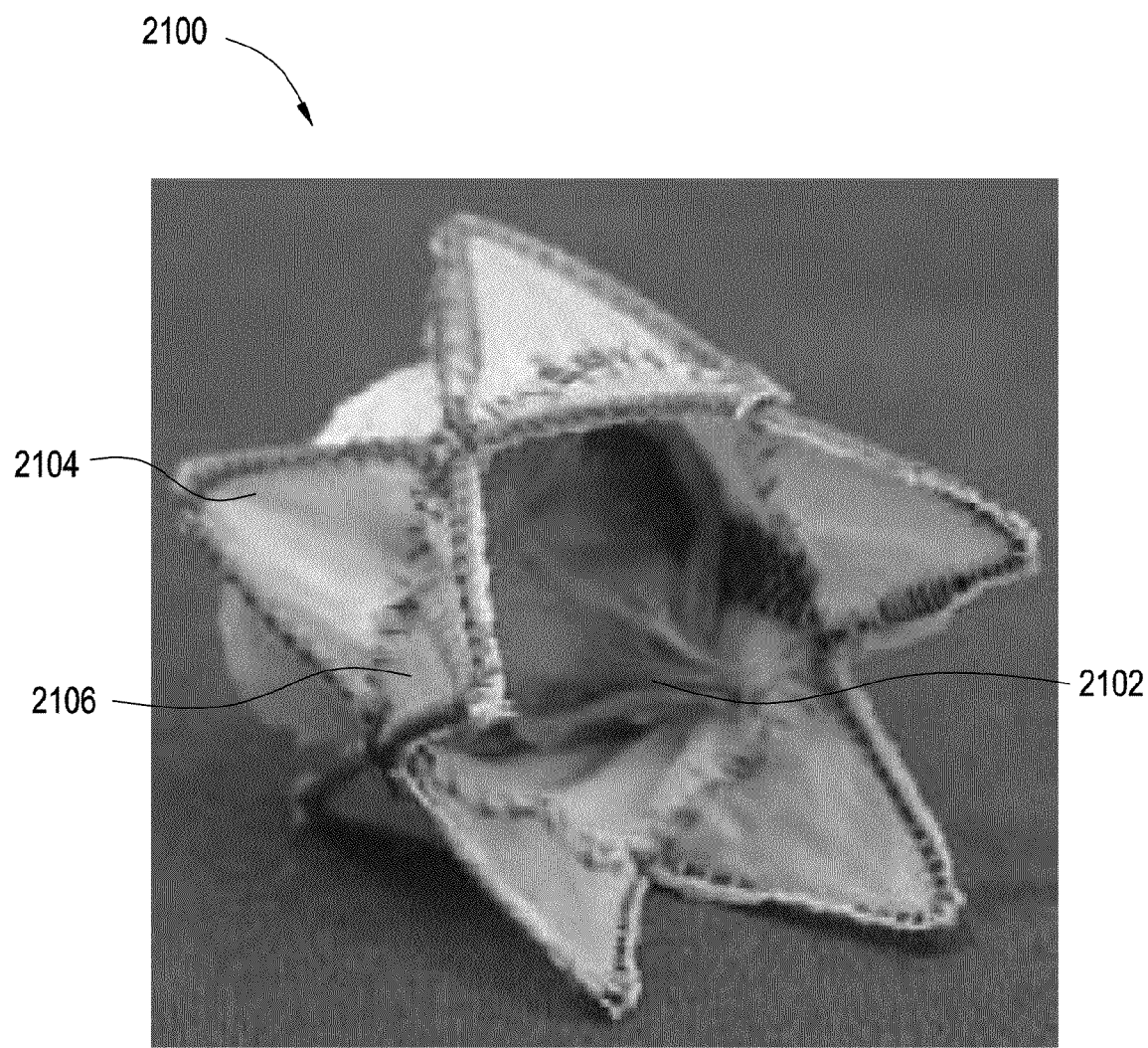
FIG. 21A shows a stent-valve in the shape of an opposed double crown according to some embodiments of the present invention.

FIG. 21A shows another example of a stent-valve 2100 in accordance with some embodiments of the present invention. The embodiment shown in FIG. 21A may be suitable for, for example, mitral valve replacement. Stent-valve 2100 may be assembled from a stent component and a valve component outside the patient's body prior to delivery of stent-valve 2100 to an implantation site. Stent-valve 2100 may be a self-expanding stent-valve adapted for replacement of the mitral valve. As shown, stent-valve 2100 may have a shape similar to an opposed double crown. Stent-valve 2100 may include a porcine pulmonary valve 2102 sutured into a Dacron conduit (prosthetic tube), with two self-expanding nitinol Z-stents 2104 and 2106 sutured on the external surface of the prosthesis in such a way to create two self-expanding crowns. The self-expanding stent-valve may be loaded for delivery into a Teflon sheath, or other suitable delivery system. In this embodiment, Dacron is used to cover the stent, although in other embodiments other materials such as Teflon, silicon, pericardium, etc. may be used. In one surgical approach, an incision of 1 centimeter may be made on the left atrium, controlled by purse string sutures. The Teflon sheath with loaded stent may be pushed along a guide wire (the atrium having been punctured with a needle and the guide wire inserted) until the middle of stent-valve reaches the mitral annulus. Then, the sheath may be pulled back to deploy the ventricular side first, followed by total removal of the sheath to expose the atrial side. Additional details regarding stent-valve 2100 and a surgical approach for delivering it to an implantation site are described in Liang Ma et al., "Double-crowned valved stents for off-pump mitral valve replacement", European Journal of Cardio-Thoracic Surgery 28:194-199, Jun. 13, 2005, which is incorporated by reference herein in its entirety.

Figure 21B:
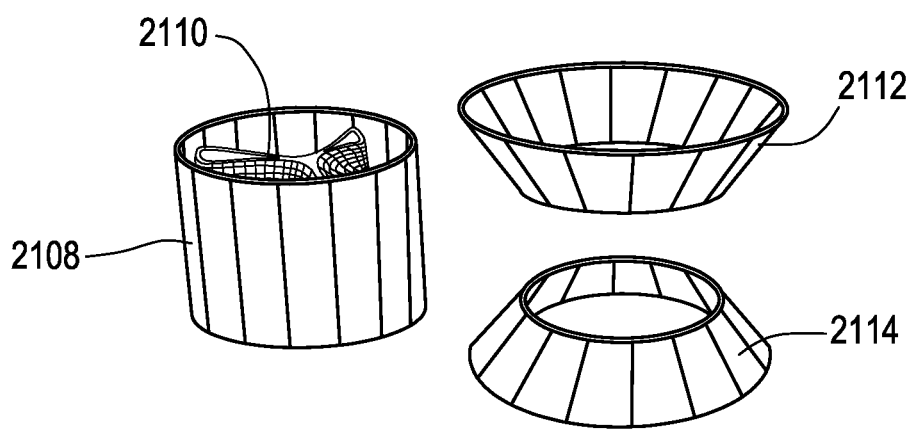
FIGS. 21B-E show views of a double-conical stent in accordance with some embodiments of the present invention.
Figure 21C:
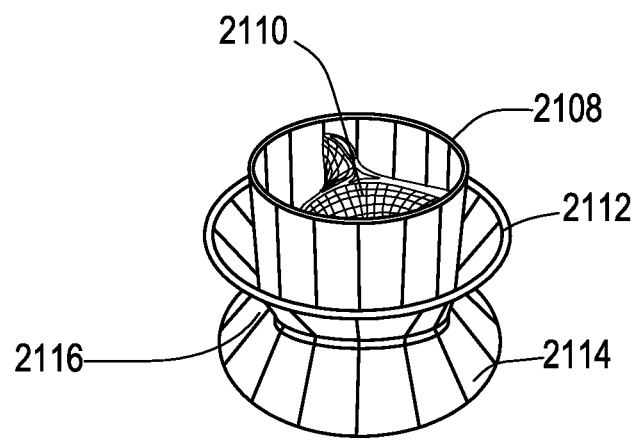
Figure 21D:
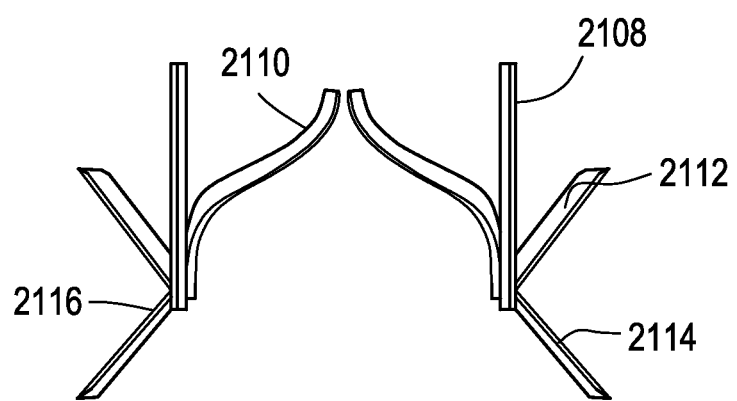
Figure 21E:
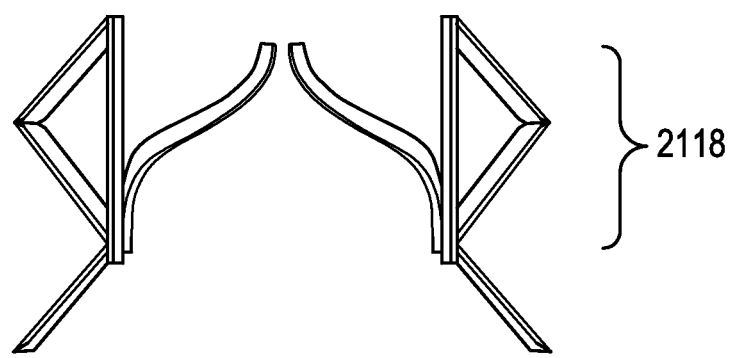

FIGS. 21B-E show views of a double-conical stent in accordance with some embodiments of the present invention. Referring to FIGS. 21B and 21C, the double-conical stent may include a substantially cylindrical stent 2108 carrying a valve 2110 as well as two substantially conical stents (2112, 2114) affixed/attached to stent 2108 (e.g., with VELCRO®, suture(s), friction fitting(s), other suitable affixing mechanism(s), or a combination thereof). FIG. 21D shows a cross-section of the double-conical stent shown in FIGS. 21B and 21C. In other embodiments, at least one of stents 2112 and 2114 may have a crown-shape with protruding spikes formed from open or closed cells or Z-stents. The first and second additional stents (2112, 2114) may collectively form a fixation element 2116 (FIG. 21C; e.g., annular groove) similar to fixation element 202 shown in FIG. 2A. Fixation element 2116 may allow for fixation, for example, in an orifice of a failed valve which is of similar size as the stent 2108 carrying valve component 2110 or to an anchoring stent with a complimentary annular projection. In some embodiments, stents 2112 and 2114 (and optionally stent 2108) may be replaced with a single stent in a double-conical configuration (e.g., the two cones connected by a continuous region in the area of fixation element 2116). An advantage to using separate stent(s) for the cones/fixation element is that the mechanical stresses of the cones/fixation element (e.g., first and second stents 2112 and 2114) can be at least partially separated from stent 2108 containing the valve. In some embodiments, at least the additional stent or portion thereof positioned closer to the tip of the delivery system (e.g., stent 2112) may be recapturable by the delivery system. To facilitate such recapturing, the additional stent may be formed in a pyramid or wing cross-sectional configuration 2118 (FIG. 21E). In some embodiments, the wing(s) or spikes of stent 2112 (and/or 2114) may be formed at various positions/heights along a central axis of stent 2108 similar to, for example, the stent shown in FIG. 7B. Having different positions/heights for at least some of the wings or spikes may facilitate engagement with, for example, native valves of different sizes. In some embodiments, the stents shown in FIGS. 21B-21E (e.g., stent 2108) may include at least one attachment element for removably attaching to a delivery device, similar to attachment elements 808 shown in FIG. 8B.

FIGS. 22A-26C show examples of delivery systems for delivering stent-valves (e.g., single-stent-valves or double-stent-valves) to an implantation site in accordance with some embodiments of the present invention. In some embodiments, the present invention provides a minimally-invasive surgical approach whereby the surgery is performed on a beating heart without the need for an open-chest cavity and heart-lung bypass. The heart may be penetrated, for example, transapically through a relatively small opening in the patient's body. For example, to replace a failed aortic valve, the patient's body may be penetrated through an intercostal space (e.g., fifth intercostal space), which is a region between two ribs. From this access point, the left ventricle may be penetrated at the apex of the heart. In one approach, a suitable stent-valve delivery system may initially penetrate the body/heart (e.g., delivery system 2600 (FIGS. 26A-26C) which includes an integrated introducer). In another approach, a separate introducer sheath may be used. A guide wire (hollow needle, catheter, stiff guide wire, etc.) may be inserted through the introducer to guide delivery of, for example, stent component(s), a valve component, and/or other devices (e.g., an occluder device). In some embodiments, transluminal, transatrial, or transventricular access approaches may be used for, for example, tricuspid and/or mitral valve replacement. The right ventricle of the heart may also be accessed for pulmonary valve replacement. This is in contrast to other surgical approaches that deliver replacement valves via open-chest cavities. Moreover, as described in greater detail below in connection with FIGS. 22A-28C, delivery systems according to some embodiments of the present invention release the proximal portion of the stent-valve first, which may allow for testing of the valve when the body is accessed, for example, trans-parietally. Upon a successful test, the distal portion of the stent-valve may be released. This contrasts with stent delivery systems that initially release the distal portions of their associated stents.

FIGS. 22A-22D show a delivery system 2200 that includes two concentrically-arranged parts, a first assembly (including elements 2202-2210) and a second assembly (including elements 2216-2230). More particularly, the first assembly may include tip 2202 at the distal end of the delivery system (with a guide wire passing through the length of the delivery system and out the tip), inner shaft 2204, outer sheath 2206, metal shaft 2208, and push handle 2210. The second assembly may include outer shaft (distal) 2216, tapered outer shaft connector 2218, outer shaft (proximal) 2220, stent holder 2222, kink protector 2224, hold handle connector 2226, hold handle cup 2228, and O-ring 2230. As shown, push handle 2210 is located at the proximal end of the delivery system. In FIGS.

22A and 22B, outer shaft 2220 has been split along its length to allow the components of delivery system 2200 to be shown in greater detail. Valve 2212 and stent(s) 2214 form a third assembly that can be, for example, loaded and crimped between the first and second assemblies.

With respect to the first assembly, inner shaft 2204 functions as a lumen for a guide wire. Tip 2202 is bonded at its distal end. As used herein, bonding refers to any suitable securing/fastening mechanism such as, for example, adhesive bonding using cyanoacrylate or UV-curing adhesives or thermal bonding/welding using heat energy to melt the components to be assembled. Outer sheath 2206 may be bonded to the proximal section of tip 2202 and may constrain the stent-valve (2212, 2214). Outer sheath 2206 may be perforated to allow device flushing via hold handle 2210. The proximal part of the first assembly may be reinforced with metal shaft 2208 and may end into the push handle with a luer connector for guide wire lumen flushing.

Figure 22D:
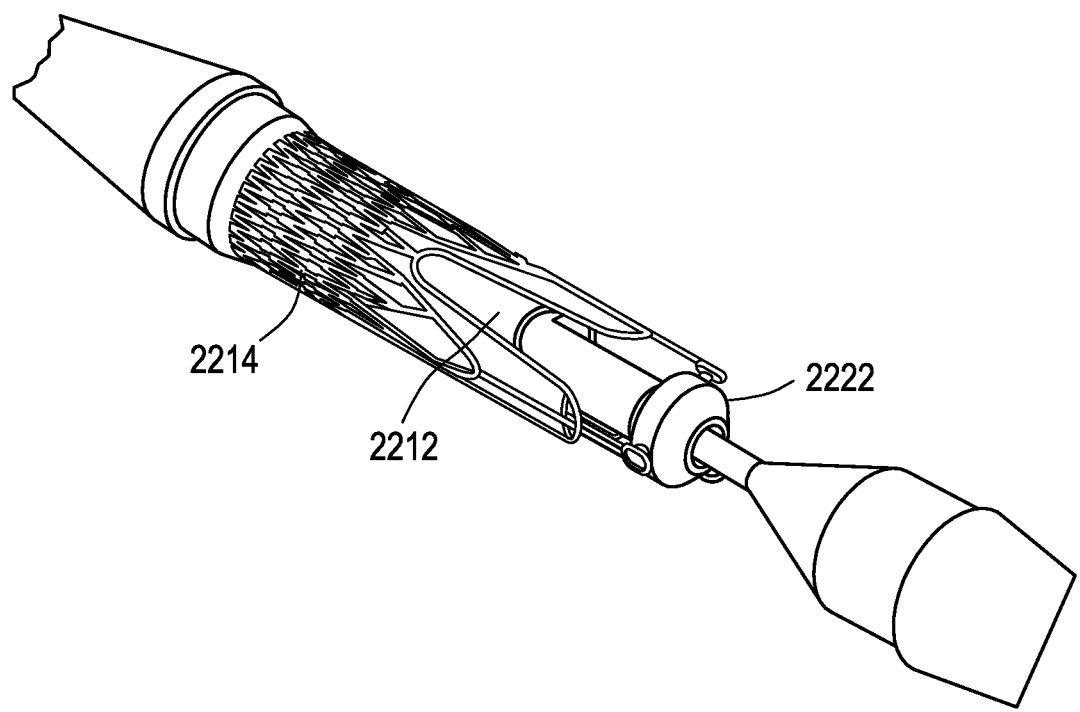

With respect to the second assembly, stent holder 2222 may be bonded distally on distal outer shaft 2216. FIG. 22D shows a perspective view better illustrating the arrangement between the stent-valve (2212, 2214) and stent holder 2222. Distal outer shaft 2216 may be bonded proximally to proximal outer shaft 2220 via tapered connector 2218. Proximal outer shaft 2220 may be bonded via kink protector 2224 to the hold handle assembly, which may include hold handle connector 2226 and hold handle cup 2228. The hold handle assembly may compress O-ring 2230 for sealing delivery system 2200. A luer connector may allow for device flushing. The flush mechanism may be used to remove trapped air from the delivery system prior to its insertion into the body. Alternatively or additionally, the flush mechanism may be used to cool down a stent (e.g., nitinol stent) prior to its release and/or recapture by flushing the stent with a cold saline solution. Cooling down the stent may cause a reversible modification of its structure, thus reducing its Young-modulus and therefore the stent radial force and the forces necessary for its delivery and recapture.

Delivery system 2200 is said to be in an open position (FIG. 22C) when (for example) push handle 2210 contacts the hold handle cup 2228. In the open position, the stent-valve (2212, 2214) may detach from stent holder 2222 and fully expand at an implantation site. Prior to delivery system 2200 reaching the open position, the stent-valve may be crimped onto delivery system 2200 by means of a crimping machine (for example) and held in place by stent holder 2222. Stent holder 2222 may affix to the attachment elements of the stents shown in FIGS. 8A-16. The crimped stent-valve may be maintained in a collapsed configuration by pulling back the first assembly thus covering the attachment components/stent holder 2222 with outer sheath 2206. Once the outer sheath 2206 is removed such that it no longer constrains the attachment components, the stent-valve may automatically detach from stent holder 2222 due to the self-expanding property of the stent-valve. Delivery system 2200 is said to be in a closed position (FIGS. 22A and 22B) when outer sheath 2206 fully encompasses the stent-valve (2212, 2214) such that no expansion of the stent-valve occurs.

Delivery system 2200 is said to be in a partially open position when (for example) push handle 2210 is partially pushed towards hold handle cup 2228. In this partially open position, the stent-valve (2212, 2214) is deployed proximally and still attached distally to stent holder 2222 via the attachment elements. This allows for an accurate implantation/positioning of the stent-valve. For example, the stent-valve may be partially released proximal to the intended implantation site and slightly pushed distally until resistance is felt. Final release of the stent-valve (2212, 2214) may occur by completely pushing the push handle towards hold handle cup 2228 so that delivery system 2200 reaches the open position. Such a partially-open position is illustrated in FIG. 28B. In some embodiments, an imaging mechanism may be used to determine whether the stent-valve is positioned correctly at the implantation site. For example, roadmapping under fluoroscopy can be realized with angiography, intra-vascular ultrasound (IVUS), intra-cardiac echocardiography (ICE), trans-esophageal echocardiography (TEE) or other mechanism(s) or combination thereof, which imaging mechanism may be at least partially integral to or separate from the delivery system.

Upon implantation of the stent-valve (2212, 2214), delivery system 2200 may revert to the closed position prior to retrieval from the patient's body, for example, by holding the first assembly and pushing the second assembly distally towards tip 2202/outer sheath 2206. In other embodiments, the handle for releasing the stent-valve may comprise a screw mechanism for transferring a rotational movement of the handle into a translational movement of the outer sheath. This type of release system may allow for stepwise, more accurate stent release and recapturing as well as a reduction of the release force felt by the surgeon.

FIGS. 23A-23D show another example of a delivery system 2300 in accordance with an embodiment of the present invention. Delivery system 2300 may be substantially similar to delivery system 2200 (FIG. 22) (e.g., closed position, FIGS. 23A and 23B; opened position, FIG. 23C), except delivery system 2300 may additionally include one or more folded balloons 2302 (e.g., proximal to the stent-valve). Unless otherwise indicated, like features in FIGS. 23A-23D correspond to the same reference numerals in FIGS. 22A-22D, although the reference numerals have not been reproduced in FIGS. 23A-23D to avoid overcomplicating the drawings. The same applies to the stent delivery systems shown in FIGS. 24A-D, FIGS. 25A-C, and FIGS. 26A-C. Balloon 2302 may be inflated/deflated via an additional lumen in proximal outer shaft 2304, for example, to anchor the stent-valve (e.g., a non-self-expanding stent-valve) in place at an implantation site. FIG. 23D shows a cross section "A-A" of the lumen structure shown in FIG. 23C. The lumen structure includes 5-lumen tubing 2306 and inner shaft 2308. In other embodiments, other structures for lumen tubing 2306 may be used (e.g., bitumen tubing where the second lumen is used for balloon inflation and deflation). Delivery system 2300 may also include access mechanism 2310 for balloon inflation/deflation, which may allow connection of a syringe or inflation device to inflate/deflate a balloon. Alternatively or additionally, tubing with an attached stop-cock may be connected to access mechanism 2310.

FIGS. 24A-24D show another example of a delivery system 2400 in accordance with an embodiment of the present invention. In delivery system 2400, proximal outer shaft 2402 may have an increased diameter in comparison to the diameter of proximal outer shaft 2220 (FIG. 22). The increased diameter may reduce bleeding when the delivery system is used without an introducer. Alternatively, when an introducer is used, the increased diameter may match the internal diameter of the introducer which, in turn, may depend on the outer diameter of the outer sheath. Having no gap between the introducer and delivery system may reduce the risk of a potential retrieval issue of the delivery system through the introducer due to entrapped blood. Accordingly, delivery system 2400 may include a floating tube 2404 that fills the gap between the inner and outer assemblies, thus reducing the risk of the inner assembly kinking under compression which would result in higher friction forces within the delivery system during stent recapturing. Delivery system 2400 may be substantially similar to delivery system 2200 in all other respects (e.g., closed position, FIGS. 24A and 24B; opened position, FIG. 24C).

FIGS. 25A-C show another example of a delivery system 2500 in accordance with an embodiment of the present invention. Delivery system 2500 may include one or more balloons 2536 distal to the stent-valve. Having the balloon(s) distal to the stent-valve avoids having to introduce the delivery system deeper into the body (e.g., into the ascending aorta) in order to perform dilation, thereby reducing risk of injury to the body and improving device handling (e.g., no bending of rigid device over the aortic arch). Balloon(s) 2536 can be used for, for example, valvuloplasty prior to stent-valve implantation and/or post-dilation of the implanted stent-valve to improve the anchoring of the stent. FIGS. 25B and 25C show the balloon(s) 2536 in closed and open positions, respectively.

The first assembly of delivery system 2500 may include tip 2502, inner balloon shaft 2504, outer sheath 2506, and floating tube 2508. The second assembly may include inner shaft (distal) 2510, stent holder transition 2512, stent holder 2514, sleeve 2516, tapered transition shaft connector 2518, and outer shaft (proximal) 2520. The handle assembly may include hold handle connector 2522, hold handle cup 2524, O-ring 2526, metal shaft 2528, and push handle 2530. The balloon assembly may include outer shaft 2532, inner shaft 2534, balloon 2536, and Y connector 2538.

FIGS. 26A-C show another example of a delivery system 2600 in accordance with an embodiment of the present invention. Delivery system 2600 may include an integrated introducer 2602, which may be an additional assembly that houses the second assembly. The outer sheath of the delivery system is shown as 2604. Introducer 2602 may include a connecting line 2606, a stopcock 2608 and a housing 2610 for the sealing membrane 2612. Stopcock 2608 may serve as an access point for, for example, a syringe containing fluid (e.g., saline). Connecting line 2606 may serve to transport the fluid from the syringe to the inner lumen of the introducer, and sealing membrane 2612 may seal the introducer from the outside environment. Upon stent-valve implantation, the components of delivery system 2600 (e.g., first assembly and second assembly) other than introducer 2602 may be retrieved through the introducer. Then, another medical device such as, for example, a closure device may be introduced through introducer 2602. Examples of closure devices are described below in connection with FIGS. 29A-33B. As another example, intravascular ultrasound (IVUS) equipment (e.g., mini-probe) may be introduced through introducer 2602. Delivery system 2600 may be substantially similar to delivery system 2200 in all other respects.

Figure 28C:
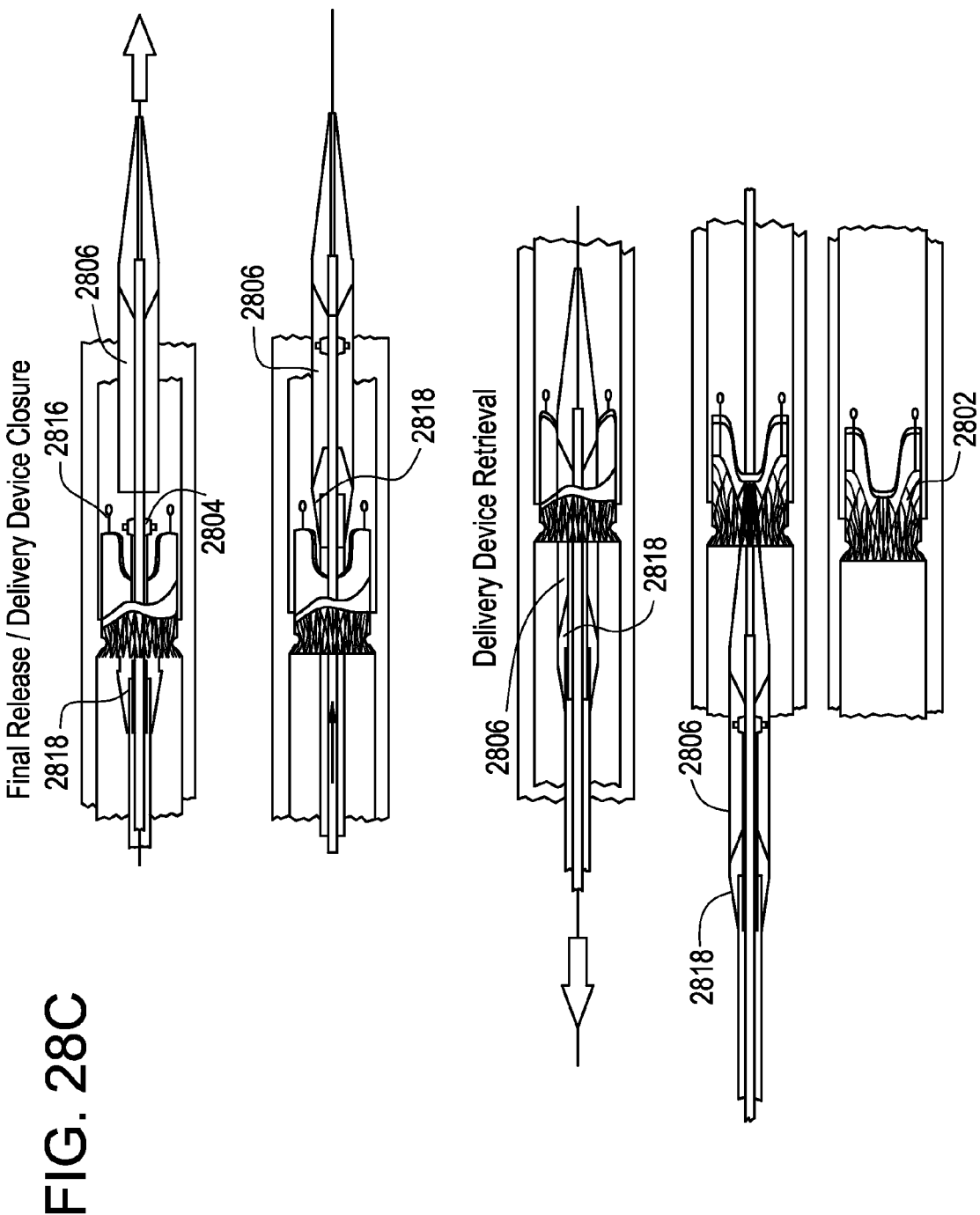

FIG. 27 is a flowchart 2700 of illustrative stages involved in replacing a failed (e.g., native or artificial) valve in accordance with some embodiments of the present invention. FIGS. 28A-28C illustrate (without limitation) various stages referenced in the flowchart of FIG. 27. At stage 2702, a stent-valve (e.g., single-stent-valve or double-stent-valve) may be removably attached to a delivery system. For example, one or more attachment elements of a stent component (e.g., attachment elements 808, FIG. 8B) may be affixed to a stent holder of the delivery device (e.g., stent holder 2222, FIG. 22). A collapsing element (e.g., outer sheath 2206, FIG. 22) may be placed over the attachment elements/stent holder to maintain the stent-valve in a collapsed configuration and attached to the delivery system.

At stage 2704, the stent-valve may be delivered to an implantation site in a collapsed configuration. For example, FIG. 28A ("introduction" and "positioning") shows that stent-valve 2802, while still attached to the delivery system via stent holder 2804 and fully contained within outer sheath 2806, may be introduced to a patient's body along guide wire 2808 so that tip 2810 of the delivery system passes through failed valve 2812. The delivery system may be manipulated forwards and/or backwards, for example, until the stent-valve is believed to be positioned correctly.

At stage 2706, the stent-valve may be partially expanded, for example, to determine (stage 2708) whether the stent-valve is in fact positioned correctly and/or to test (stage 2710) whether the stent-valve is functioning properly. For example, FIG. 28A ("partial release") shows that outer sheath 2806 may be partially removed from proximal section 2814 of the stent-valve, while attachment elements 2816 of the stent-valve are still constrained by outer sheath 2806 onto stent holder 2804.

At stage 2712, when the stent-valve is positioned correctly at the implantation site and/or the stent-valve is functioning properly, the stent-valve may be detached from the delivery system in order to cause the stent-valve to expand to its fully-expanded configuration. For example, FIG. 28C ("final release") shows that, upon removal of attachment elements 2816 and stent holder 2804 from within outer sheath 2806, attachment elements 2816 of stent-valve 2802 may detach from stent holder 2804 automatically (or in response to balloon inflation in other embodiments) thereby causing the stent-valve to expand to its fully-expanded configuration. The second assembly of the delivery device may then be reunited with the first assembly/outer sheath and removed from the patient's body. For example, FIG. 28C ("delivery device retrieval") shows that the second assembly 2818 may be passed through replacement stent-valve 2802 towards the distal end of the stent-valve. Then, the reunited second assembly 2818 and first assembly/outer sheath 2806 may be passed through stent-valve 2802 again in the proximal direction before exiting the patient's body.

When the stent-valve is not positioned correctly (stage 2708), at stage 2714 the stent-valve may be reverted to the collapsed configuration and repositioned within the patient's body. An illustration of this scenario is illustrated in FIG. 28B ("stent recapturing/repositioning"), in which outer sheath 2806 is slid in the proximal direction over proximal section 2814 of the stent-valve in order to recapture the stent-valve. The stent-valve is then repositioned and released such that fixation element 2820 of the stent-valve receives an annulus 2822 of the failed valve. Similarly, when the stent-valve malfunctions in response to a test (stage 2710), at stage 2716 the stent-valve may be reverted to the collapsed configuration and removed from the patient's body.

FIGS. 29A-33B show illustrative embodiments of guide wire compatible closure (occluder) devices for sealing access orifices and associated surgical instruments in accordance with some embodiments of the present invention. Such an occluder may repair, for example, a cardiac access orifice (e.g., ventricular orifice) used for valve replacement. The occluder may be introduced to a patient's body after a replacement valve has been implanted (or removed due to malfunction or complication during installation). Embodiments of the present invention address shortcomings with conventional closure devices, such as the looseness of their fit. Conventional closure devices also lack a central lumen, which renders them incompatible with guide wire delivery systems.

Figure 29A:
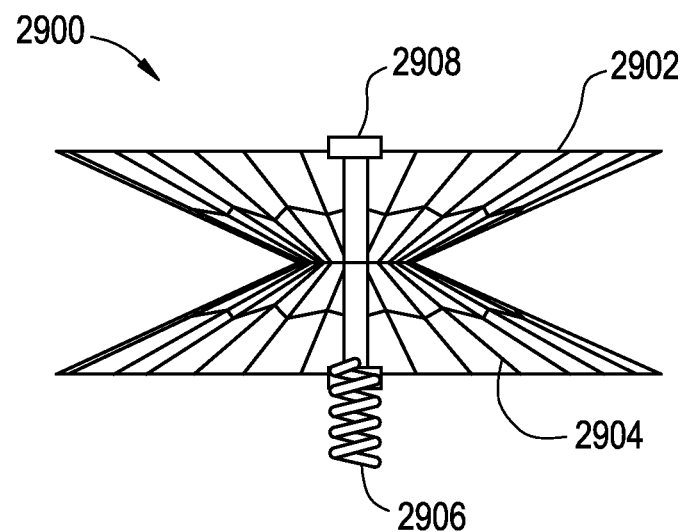
FIGS. 29A and 29B show a guide wire compatible occluder for sealing an access orifice according to some embodiments of the present invention.
Figure 29B:
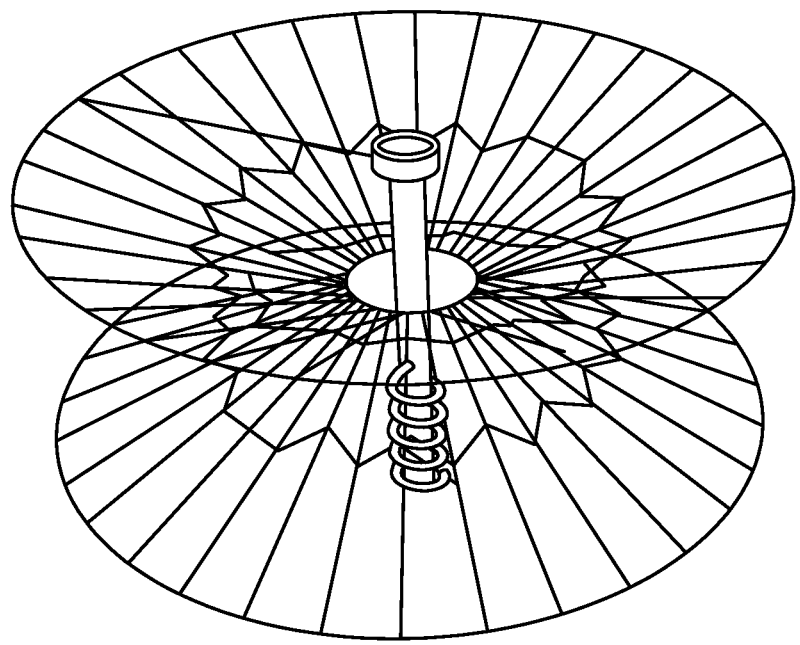

FIGS. 29A and 29B are side and perspective views of an occluder 2900 in accordance with some embodiments of the present invention. Occluder 2900 may include stainless steel wire, nitinol, textile fibers, fills, biocompatible materials, and/or other suitable materials which allow the device to perform as intended. In some embodiments, at least a portion of occluder 2900 may be fitted/filled with a flexible but tight material such as, for example, a membrane or foam. Occluder 2900 may or may not include a skeleton (e.g., lattice structure with a filling material) and/or sealing membranes. Such a skeleton may comprise nitinol, stainless steel, magnesium, nylon, polyester, polypropylene, polydioxanon, other suitable material(s), or a combination thereof. The filling material may include, for example, polyester, polyurethane, gelatin, other suitable material(s), or a combination thereof. When occluder 2900 includes a sealing mechanism, such a mechanism may be flexible such that it does not interfere with the expanding or collapsing of occluder 2900 (described below) according to some embodiments of the present invention.

Top portion 2902 of occluder 2900 may be positioned on the luminal side of an access orifice, while bottom portion 2904 may be positioned outside the access orifice. Guide wire compatibility may be achieved through a central channel within occluder 2900. The central channel may include at its bottom end, for example, a hollow screw device 2906 for attaching occluder 2900 to a catheter during delivery and detaching the occluder from the catheter upon installation within the access orifice. In other embodiments, occluder 2900 may be attached/detached to a catheter by a thin wall that can be twisted off, by a connection mechanism in the shape of a hook, or by a mechanism that detaches via galvanic corrosion or the like.

Occluder 2900 may include a channel sealing mechanism 2908 such as, for example, a self-sealing membrane and/or foam. In some embodiments, channel sealing mechanism 2908 may include a valve (e.g., one or more plastic leaflets). Channel sealing mechanism 2908 may prevent blood-flow through the occluder from top/luminal portion 2902 to bottom portion 2904 after the occluder is installed within the access orifice. During delivery, the positioning of a guide wire through channel sealing mechanism 2908 (and the central channel) may or may not substantially or entirely prevent blood-flow through channel sealing mechanism 2908. In some embodiments, mechanism 2908 may rely, at least in part, on blood clotting in order to form a seal. In some embodiments, mechanism 2908 (including a membrane, an iris mechanism, or collapsible walls) may form the seal (with or without assistance from blood clotting).

In some embodiments, top/luminal portion 2902 of occluder 2900 may be made from different material(s) (or the same material(s) but having different characteristics) than the material(s) used for bottom/outer portion 2904. For example, bottom/outer portion 2904 made be made from a coarser or more porous material than top/luminal portion 2902 to facilitate the formation of scar tissue on the outer portion. Bioabsorbable material(s) may also be used for portion 2902 and/or 2904 of occluder 2900 (e.g., magnesium and/or polydioxanone for a skeleton portion and/or polydioxanone, polyhydroxybutyrate, and/or gelatin as a filler).

Figure 30:
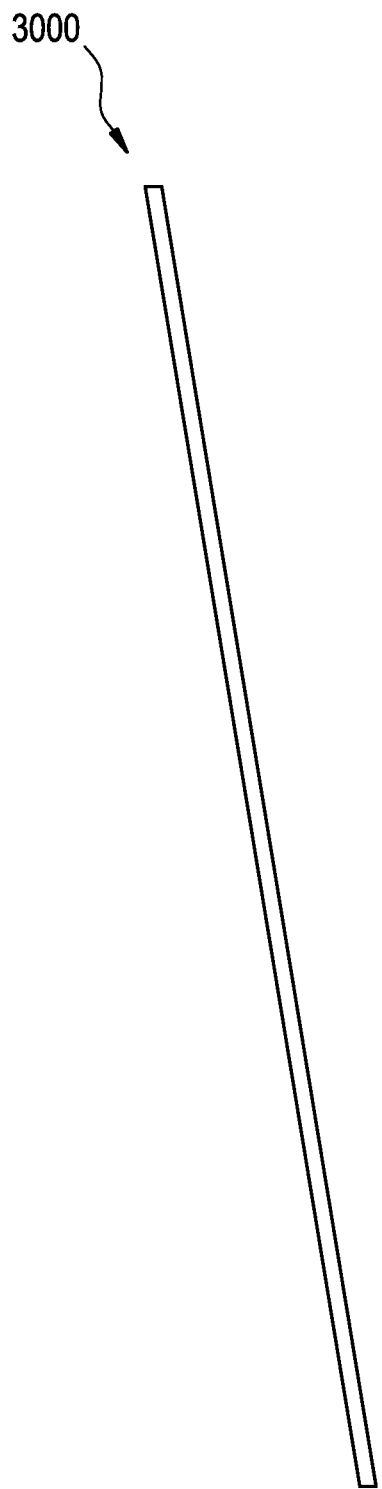
FIG. 30 shows a guide wire for guiding the delivery of an occluder and/or stent-valve according to some embodiments of the present invention.
Figure 31:
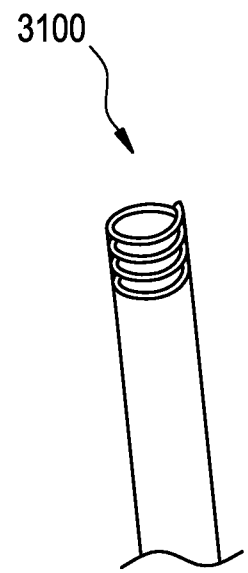
FIG. 31 shows a threaded catheter for attachment to and use in positioning an occluder according to some embodiments of the present invention.

FIG. 30 shows a perspective view of a guide wire 3000 for guiding the delivery of occluder 2900 to the access orifice. Guide wire 3000 may be the same guide wire used, for example, for a valve replacement surgery involving one of the delivery systems shown in FIGS. 22A-26C. FIG. 31 shows a perspective view of a threaded catheter 3100 for attaching to occluder 2900 during delivery and detaching from occluder 2900 once installation of the occluder is complete. As shown in FIGS. 32A and 32B, screw device 2906 of occluder 2900 may attach to threaded catheter 3100, and occluder 2900 may be loaded into second catheter 3202. For example, second catheter 3202 may be part of the delivery system (e.g., FIG. 26A-C) used for delivery of a replacement valve. Guide wire 3000 may extend through both the central channel of occluder 2900 and second catheter 3200. Guide wire 3000 may also be removable and reinsertable. FIG. 32B shows that the occluder can be partially unloaded by moving catheter 3100 relative to catheter 3202. Advantageously, if occluder 2900 is not positioned correctly upon partial release, it can be reloaded into catheter 3202 and relocated to the proper location within the access orifice without excessive manipulation of occluder 2900 and/or the associated delivery instruments.

Figure 33A:
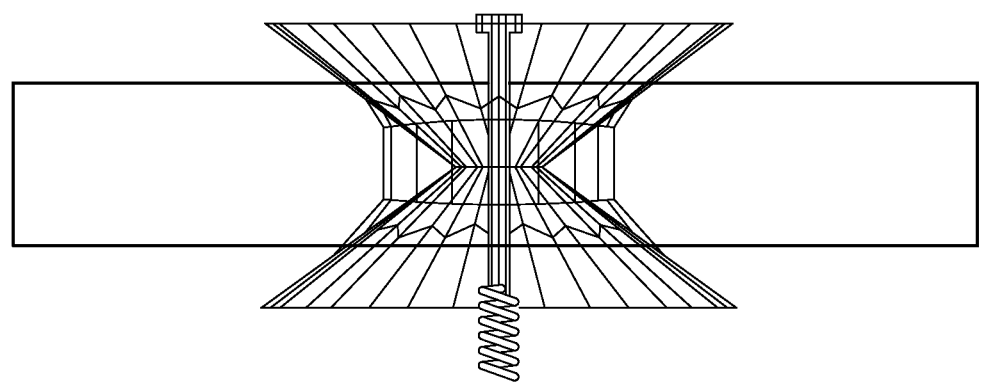
FIGS. 33A and 33B show an occluder positioned within an access orifice according to some embodiments of the present invention.
Figure 33B:
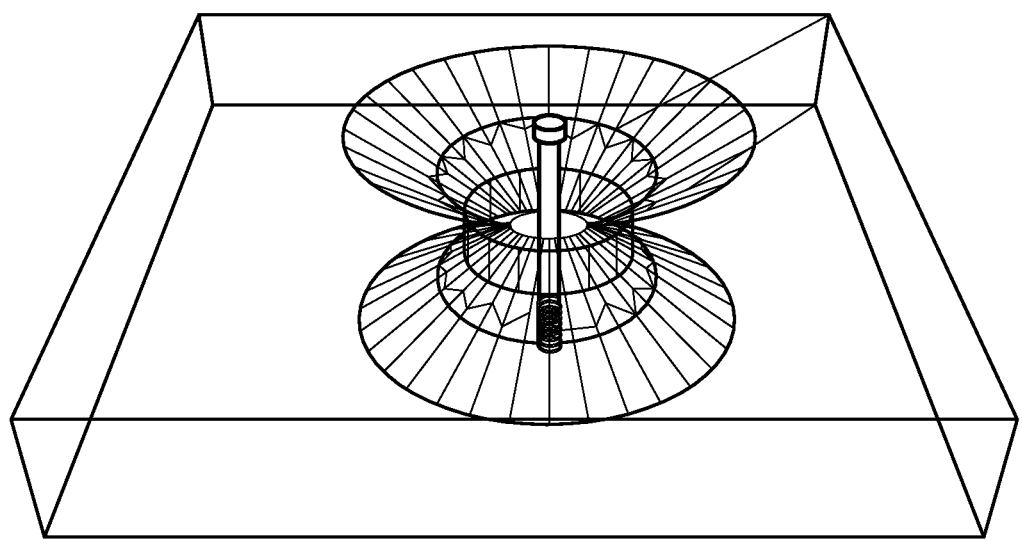

FIGS. 33A and 33B illustrate side and perspective views of occluder 2900 in an expanded configuration within an access orifice in accordance with an embodiment of the present invention. Preferably, luminal/top portion 2902 and outer/bottom portion 2904 of occluder 2900 cover the access orifice completely. The central channel is also preferably sealed by, for example, a self-sealing membrane and/or sealing foam 2908.

Thus it is seen that stent-valves (e.g., single-stent-valves and double-stent-valves) and associated methods and systems for surgery are provided. Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The inventors reserve the right to pursue such inventions in later claims.

What is claimed is:
1. A cardiac stent-valve delivery system comprising:
a stent-valve having a proximal section and at least one attachment element at a distal section and the stent-valve configured to be expandable between a first constrained, collapsed configuration and a second unconstrained expanded configuration;
a first assembly comprising an outer sheath and a guide wire tube;
a tip at a distal end of the delivery system, for passing a guide wire through the length of the delivery system and out of the tip via the guide wire tubing, the distal end of the delivery system configured for introduction in a patient's body along the guide wire so that the tip at the distal end passes through a failed valve at an implantation site for the stent-valve; and
a second assembly comprising a stent holder configured for removable attachment to the at least one attachment element of the stent-valve, the stent-valve positioned over the guide wire tube of the first assembly and having the proximal section arranged toward a proximal end of the delivery system, and the distal section arranged toward the distal end of the delivery system,
wherein
the first assembly and the second assembly are configured for relative movement with respect to one another in order to transition from a closed position to an open position, such that in the closed position, the outer sheath encompasses and constrains an entirety of the stent-valve in the first constrained, collapsed configuration, in the open position the outer sheath does not constrain the stent-valve and the stent-valve is released and detaches from the stent holder and expands to the second unconstrained expanded configuration, and relative movement between the first assembly and the second assembly is configured such that upon transition from the closed position to the open position, the outer sheath is translated in a distal direction such that the proximal section of the stent-valve is released prior to release of the distal section of the stent-valve.

2. The stent-valve delivery system of claim 1, wherein the first assembly and the second assembly are configured to transition from the closed position, to a partially-open position, to the open position, wherein in the partially-open position, the proximal section of the stent-valve expands partially but does not detach from the stent holder because the outer sheath still encompasses the at least one attachment element of the stent-valve and the stent holder.

3. The stent-valve delivery system of claim 2, further comprising a flush mechanism.

4. The stent-valve delivery system of claim 1, further comprising a push handle for causing the relative movement of the first assembly and the second assembly.

5. The stent-valve delivery system of claim 1, further comprising a screw mechanism for translating rotational movement of a handle into the relative movement of the first assembly and the second assembly.

6. The stent-valve delivery system of claim 1, further comprising an integrated introducer within which the first assembly and the second assembly are positioned during delivery of the stent-valve to the implantation site, wherein the integrated introducer is configured to remain within the patient's body even after the first assembly and the second assembly are removed.

7. The stent-valve delivery system of claim 1, wherein after expansion of the stent-valve to the second unconstrained expanded configuration, the second assembly is configured to be passed through the stent-valve towards a distal end of the first assembly.

8. The stent-valve delivery system of claim 7, wherein the first assembly and the second assembly are configured to be passed through the stent-valve in a proximal direction after expansion and release of the stent-valve before exiting the patient's body.

9. The stent-valve delivery system of claim 1, wherein the at least one attachment element of the stent-valve comprises a geometrical opening configured for removable attachment to a complimentary structure of the stent holder.

10. The stent-valve delivery system of claim 9, wherein the geometrical opening comprises a circular or ovular opening.

11. The stent-valve delivery system of claim 1, wherein the at least one attachment element of the stent-valve comprises a wire, hook, or strap configured for removable attachment to a complimentary structure of the stent holder.

12. The stent-valve delivery system of claim 1, wherein the at least one attachment element of the stent-valve comprises at least two attachment elements configured for removable attachment to corresponding number of complimentary structures of the stent holder.

13. The stent-valve delivery system of claim 1, wherein the at least one attachment element of the stent-valve comprises at least three attachment elements configured for removable attachment to corresponding number of complimentary structures of the stent holder.

14. The stent-valve delivery system of claim 1, wherein the at least one attachment element of the stent-valve comprises at least six attachment elements configured for removable attachment to corresponding number of complimentary structures of the stent holder.

15. The stent-valve delivery system of claim 1, wherein the stent-valve comprises a lattice structure comprising: at least one commissural post; and the at least one attachment element.

16. The stent-valve delivery system of claim 15, wherein the lattice structure of the stent-valve further comprises a supporting element for connecting the at least one commissural post to the at least one attachment element.

17. The stent-valve delivery system of claim 1, wherein the stent-valve includes a stent component which comprises a lattice structure with a plurality of cells, all of the cells being closed cells to facilitate recapture of the stent-valve from a partially expanded configuration to a collapsed condition by sliding the outer sheath in a proximal direction over the proximal section of the stent-valve.

18. The stent-valve delivery system of claim 1, wherein the first assembly and the second assembly are configured for accessing the patient's body through an intercostal space and penetrating the left ventricle at the apex of the heart.

19. The stent-valve delivery system of claim 1, wherein the stent-valve comprises a stent component and a valve component, the stent component comprising a first section including a fixation element, a second section for housing the valve component, and a third section, wherein the third section includes the at least one attachment element configured for removable attachment to the stent holder.

20. The stent-valve delivery system of claim 19, wherein the third section has a diameter that is less than a diameter of the second section.

21. The stent-valve delivery system of claim 19, wherein the fixation element comprises an annular groove.

22. The stent-valve delivery system of claim 21, wherein the annular groove is formed from a plurality of independently bendable elements, wherein each bendable element comprises a bending deformation, a location of which is determined by the lengths of an attached pair of struts.

23. A cardiac stent-valve delivery system comprising:
a stent-valve having a proximal section and at least one attachment element at a distal section, and the stent-valve configured to be expandable between a first constrained collapsed configuration and a second unconstrained expanded configuration;
a first assembly comprising an outer sheath and a guide wire tube;
a tip at a distal end of the delivery system, for passing a guide wire through the length of the delivery system and out of the tip via the guide wire tube, the distal end of the delivery system configured for introduction in a patient's body along the guide wire so that the tip at the distal end passes through a failed valve at an implantation site for the stent-valve; and
a second assembly comprising a stent holder configured for removable attachment to the at least one attachment element of the stent-valve, the stent-valve positioned over the guide wire tube of the first assembly and having the proximal section arranged toward a proximal end of the delivery system, and the distal section arranged toward the distal end of the delivery system, wherein
the first assembly and the second assembly are configured for relative movement with respect to one another in order to transition from a closed position to a partially-open position, to an open position, such that in the closed position, the outer sheath encompasses and constrains an entirety of the stent-valve in the first constrained, collapsed configuration, in the open position the outer sheath does not constrain the stent-valve and the stent-valve is released and detaches from the stent holder and expands to the second unconstrained expanded configuration, and relative movement between the first assembly and the second assembly is configured such that upon transition from the closed position towards the open position, the proximal section of the stent-valve is released first, and in the partially-open position, the proximal section of the stent-valve expands partially but does not detach from the stent holder due to the outer sheath still encompassing the at least one attachment element of the stent-valve and the stent holder.

24. The stent-valve delivery system of claim 23, further comprising a flush mechanism.

25. The stent-valve delivery system of claim 23, further comprising a push handle for causing the relative movement of the first assembly and the second assembly.

26. The stent-valve delivery system of claim 23, further comprising a screw mechanism for translating rotational movement of a handle into the relative movement of the first assembly and the second assembly.

27. The stent-valve delivery system of claim 23, wherein after expansion of the stent-valve to the second unconstrained expanded configuration, second assembly is configured to be passed through the stent-valve towards a distal end of the first assembly.

28. The stent-valve delivery system of claim 27, wherein the first assembly and the second assembly are configured to be passed through the stent-valve in a proximal direction before exiting the patient's body.

29. The stent-valve delivery system of claim 23, wherein the at least one attachment element of the stent-valve comprises a geometrical opening configured for removable attachment to a complimentary structure of the stent holder.

30. The stent-valve delivery system of claim 29, wherein the geometrical opening comprises a circular or ovular opening.

31. The stent-valve delivery system of claim 23, wherein the at least one attachment element of the stent-valve comprises at least two attachment elements configured for removable attachment to corresponding number of complimentary structures of the stent holder.

32. The stent-valve delivery system of claim 23, wherein the at least one attachment element of the stent-valve comprises at least three attachment elements configured for removable attachment to corresponding number of complimentary structures of the stent holder.

33. The stent-valve delivery system of claim 23, wherein the stent-valve comprises a lattice structure comprising: at least one commissural post; and the at least one attachment element.

34. The stent-valve delivery system of claim 33, wherein the lattice structure of the stent-valve further comprises a supporting element for connecting the at least one commissural post to the at least one attachment element.

35. The stent-valve delivery system of claim 23, wherein the stent-valve includes a stent component which comprises a lattice structure with a plurality of cells, all of the cells being closed cells to facilitate recapture of the stent-valve from partially expanded configuration to a collapsed condition by sliding the outer sheath in a proximal direction over the proximal section of the stent-valve.

36. The stent-valve delivery system of claim 23, wherein the first assembly and the second assembly are configured for accessing the patient's body through an intercostal space and penetrating the left ventricle at the apex of the heart.

37. The stent-valve delivery system of claim 23, wherein the stent-valve comprises a stent component and a valve component, the stent component comprising a first section including a fixation element, a second section for housing the valve component, and a third section, wherein the third section includes the at least one attachment element configured for removable attachment to the stent holder.

* * * * *